United States Patent [19]
Raines et al.

[11] Patent Number: 5,618,268
[45] Date of Patent: Apr. 8, 1997

[54] MEDICAL INFUSION DEVICES AND MEDICINE DELIVERY SYSTEMS EMPLOYING THE SAME

[75] Inventors: Kenneth C. Raines; Gary Fenicle, both of Bethlehem, Pa.

[73] Assignee: B. Braun Medical Inc., Allentown, Pa.

[21] Appl. No.: 470,253

[22] Filed: Jun. 6, 1995

[51] Int. Cl.⁶ .................................................. A61M 5/00
[52] U.S. Cl. ............................. 604/82; 604/83; 604/247
[58] Field of Search ................................. 604/82, 83, 245, 604/246, 247, 249, 236, 48, 49; 137/605, 606, 112, 512.4

[56] References Cited

U.S. PATENT DOCUMENTS

| | | |
|---|---|---|
| 4,210,173 | 7/1980 | Choksi et al. . |
| 4,222,407 | 9/1980 | Ruschke et al. . |
| 4,244,378 | 1/1981 | Brignola . |
| 4,246,932 | 1/1981 | Raines . |
| 4,274,445 | 6/1981 | Cooper . |
| 4,310,017 | 1/1982 | Raines . |
| 4,354,492 | 10/1982 | McPhee . |
| 4,429,856 | 2/1984 | Jackson . |
| 4,506,691 | 3/1985 | Tseo . |
| 4,535,820 | 8/1985 | Raines . |
| 4,556,086 | 12/1985 | Raines . |
| 4,610,276 | 9/1986 | Paradis et al. . |
| 4,666,429 | 5/1987 | Stone . |
| 4,683,916 | 8/1987 | Raines . |
| 4,762,149 | 8/1988 | Pickl, Jr. . |
| 4,765,372 | 8/1988 | Beecher . |
| 4,819,684 | 4/1989 | Zaugg et al. ............................ 137/112 |
| 4,908,018 | 3/1990 | Thomsen . |
| 4,915,687 | 4/1990 | Sivert . |
| 5,127,904 | 7/1992 | Loo et al. ................................. 604/83 |
| 5,184,652 | 2/1993 | Fan ..................................... 604/249 X |
| 5,190,067 | 3/1993 | Paradis et al. ....................... 604/83 X |
| 5,431,185 | 7/1995 | Shannon et al. .................... 604/247 X |

*Primary Examiner*—John D. Yasko
*Attorney, Agent, or Firm*—Hopgood, Calimafde, Kalil & Judlowe L.L.P.

[57] ABSTRACT

In general, the medical infusion device of the present invention includes at least one check valve chamber through which a primary intravenous stream is arranged to pass by way of a primary fluid inlet port and a primary outlet port. Each check valve chamber has at least one physically associated infusion port through which a medicational or nutritional fluid can be injected in any number of possible ways. Each check valve chamber has an interior volume, a check valve opening formed between its interior volume and its associated infusion port, a check valve chamber opening formed through the check valve chamber and axially aligned with the check valve opening, a flexible check valve element, and a check valve support element. The check valve support element is installed through the check valve chamber opening and is mounted within the check valve chamber so as to support the flexible check valve element over the check valve opening in a normally closed configuration, and thus prevents fluid from passing therethrough. By virtue of this novel construction, medicational or nutritional fluids can now, be easily injected into the infusion port of the medical infusion device and directly infused into the primary intravenous stream flowing through its check valve chamber with minimal loss of injected fluid.

86 Claims, 19 Drawing Sheets

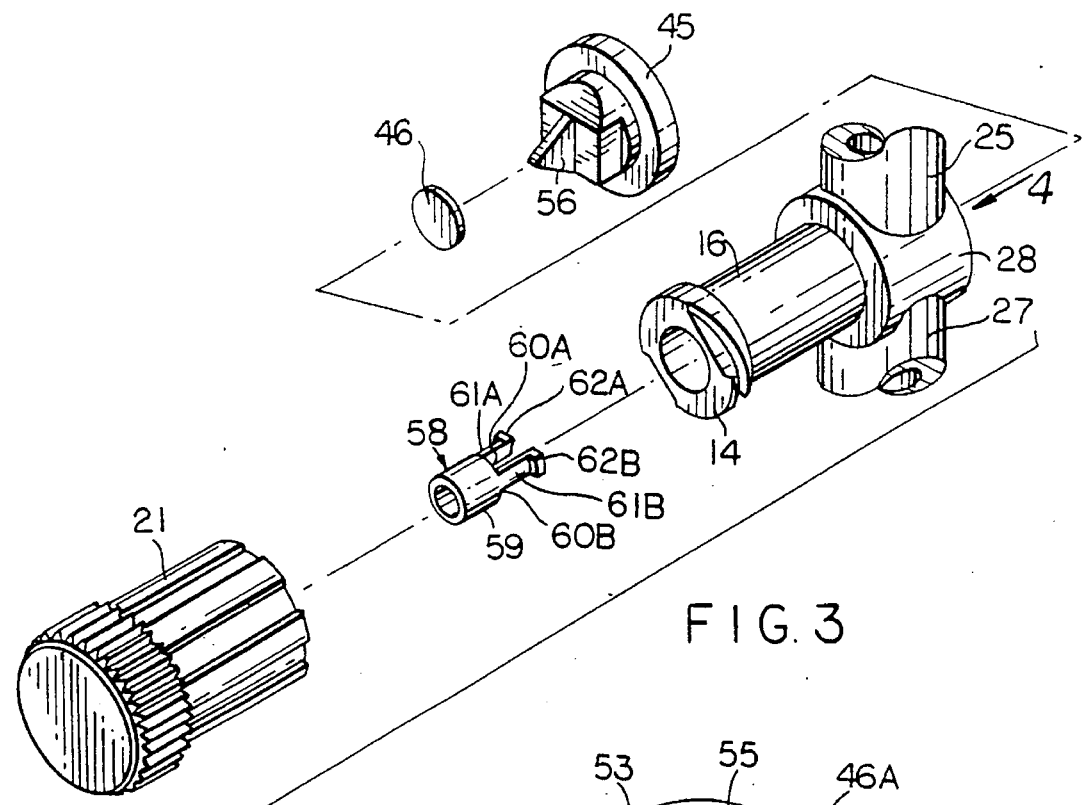
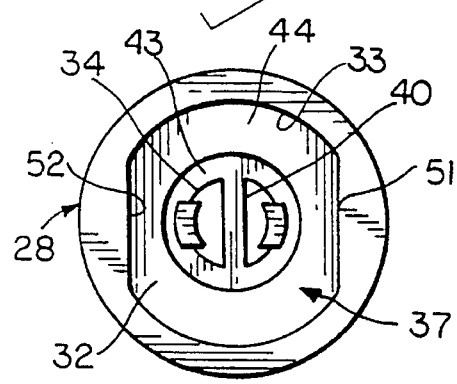
FIG. 4
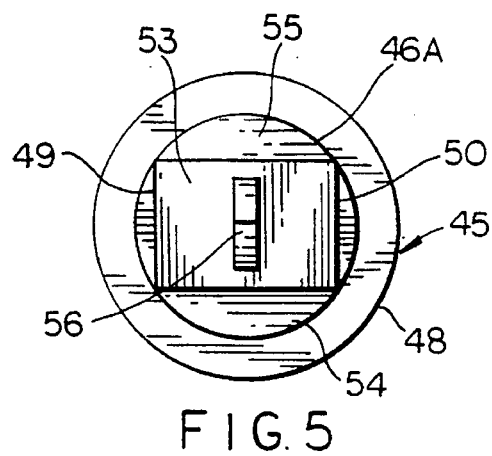
FIG. 5
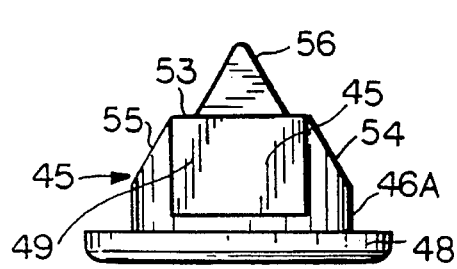
FIG. 6
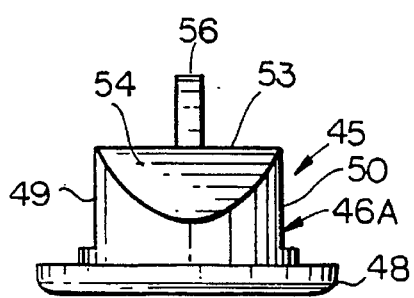
FIG. 7

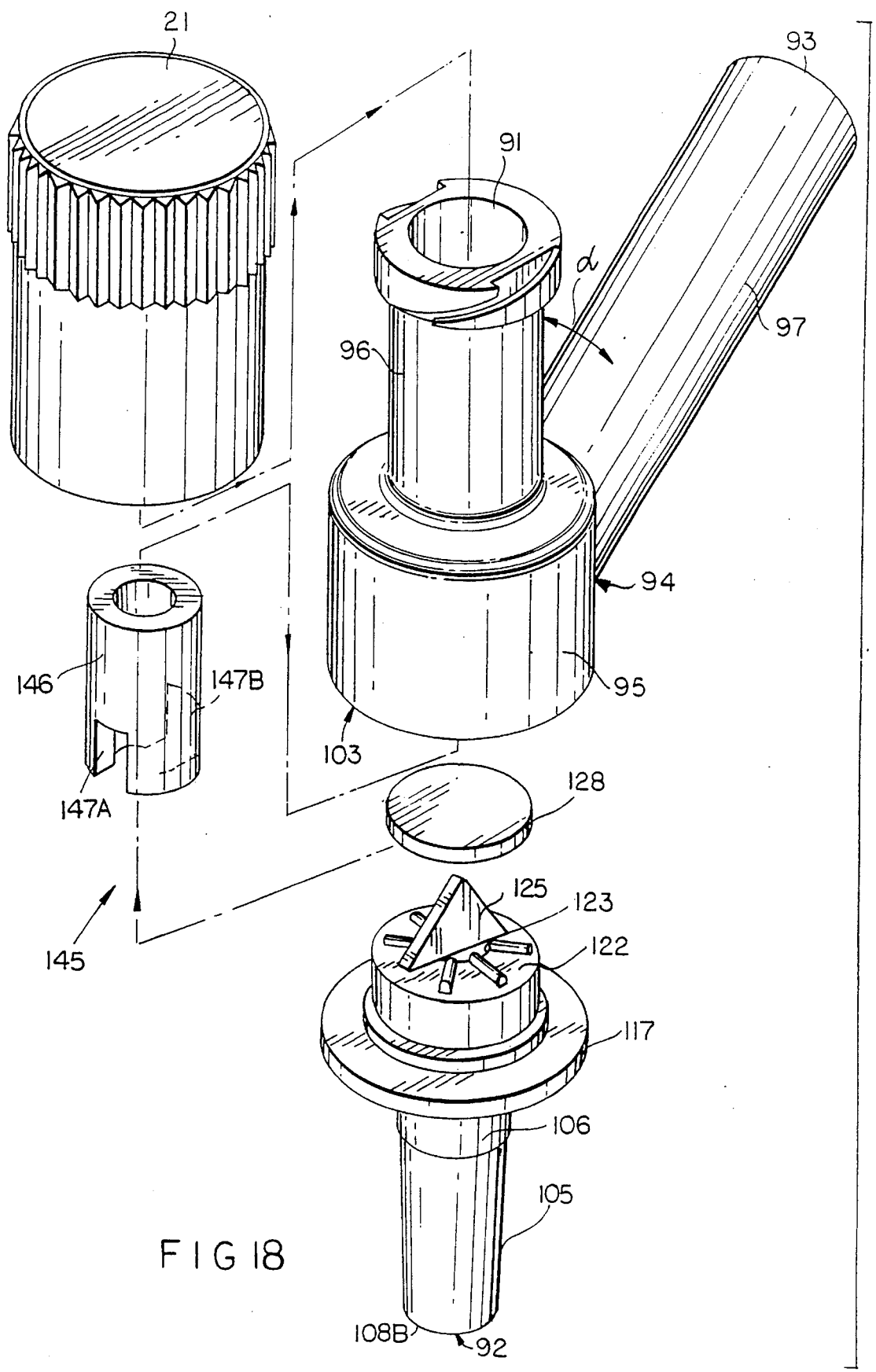

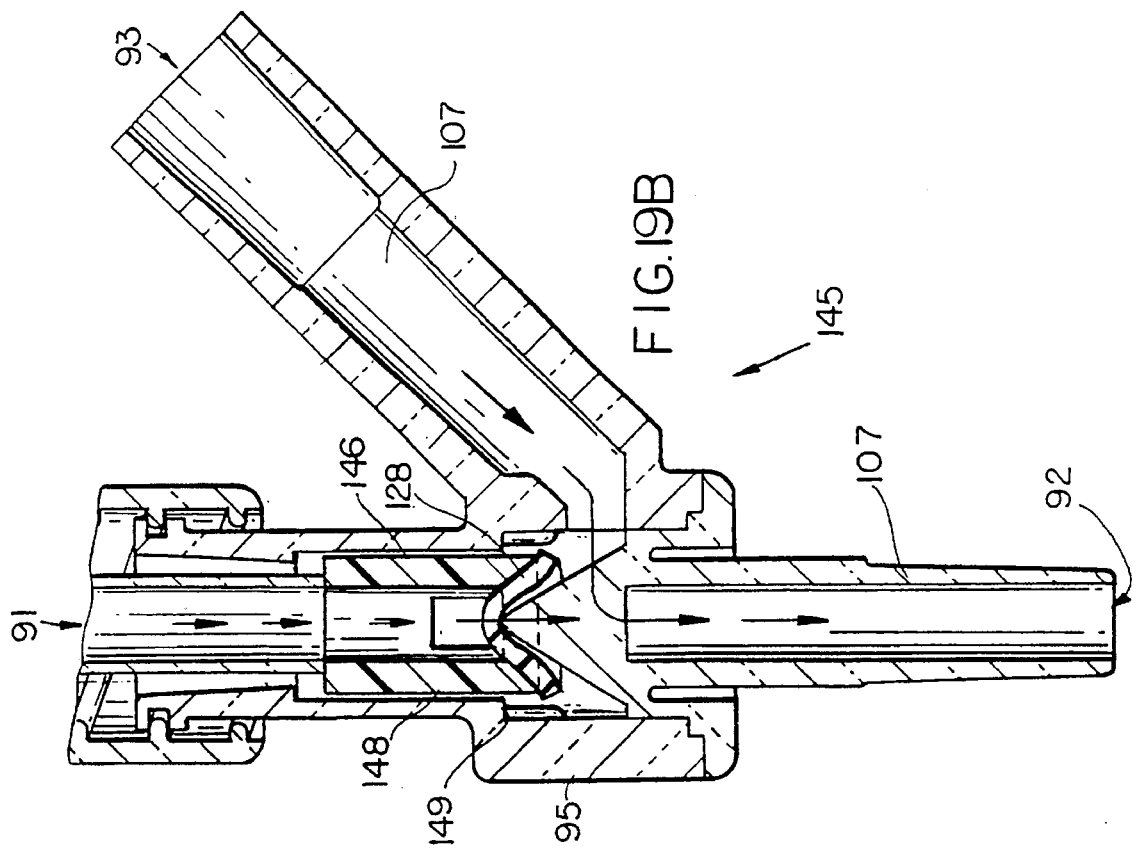
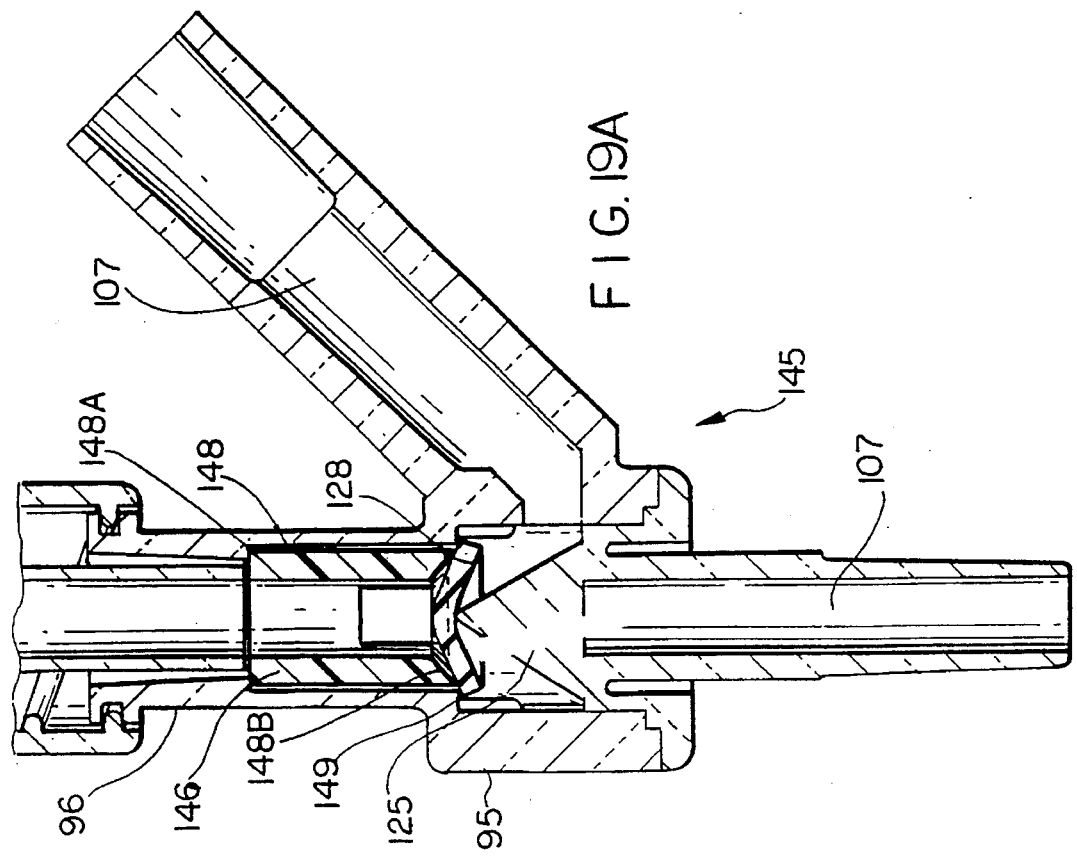

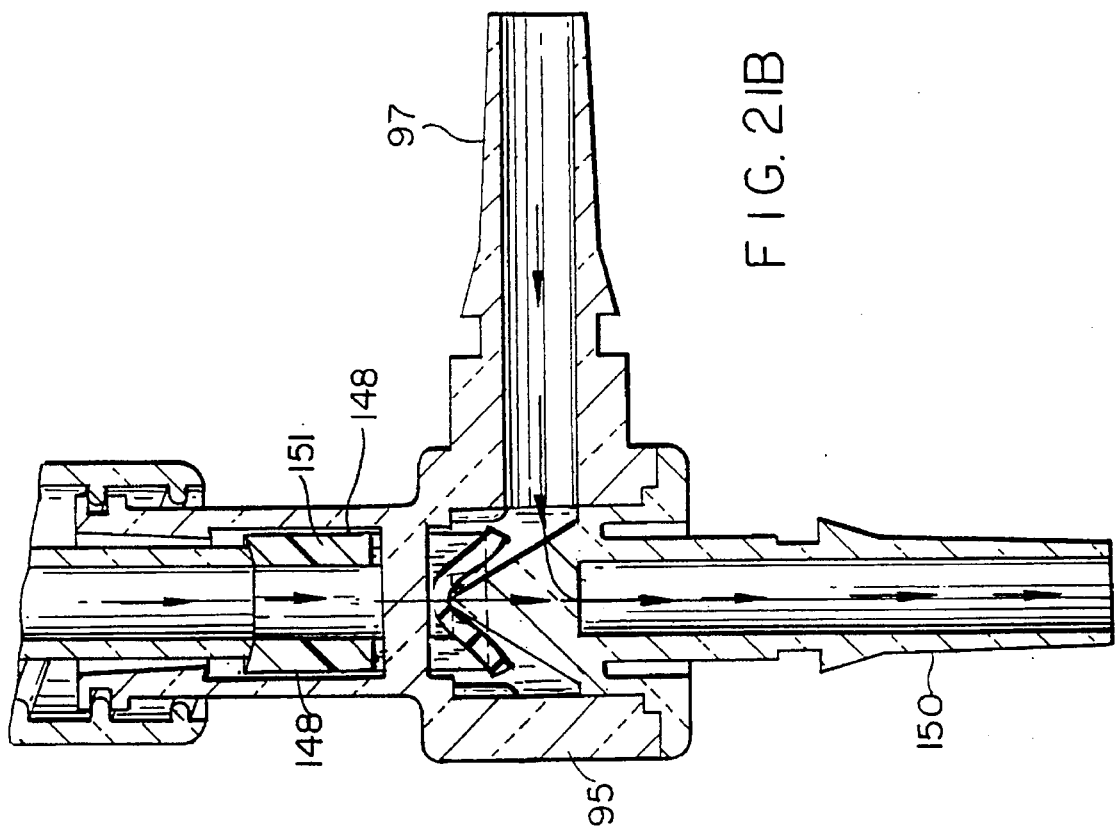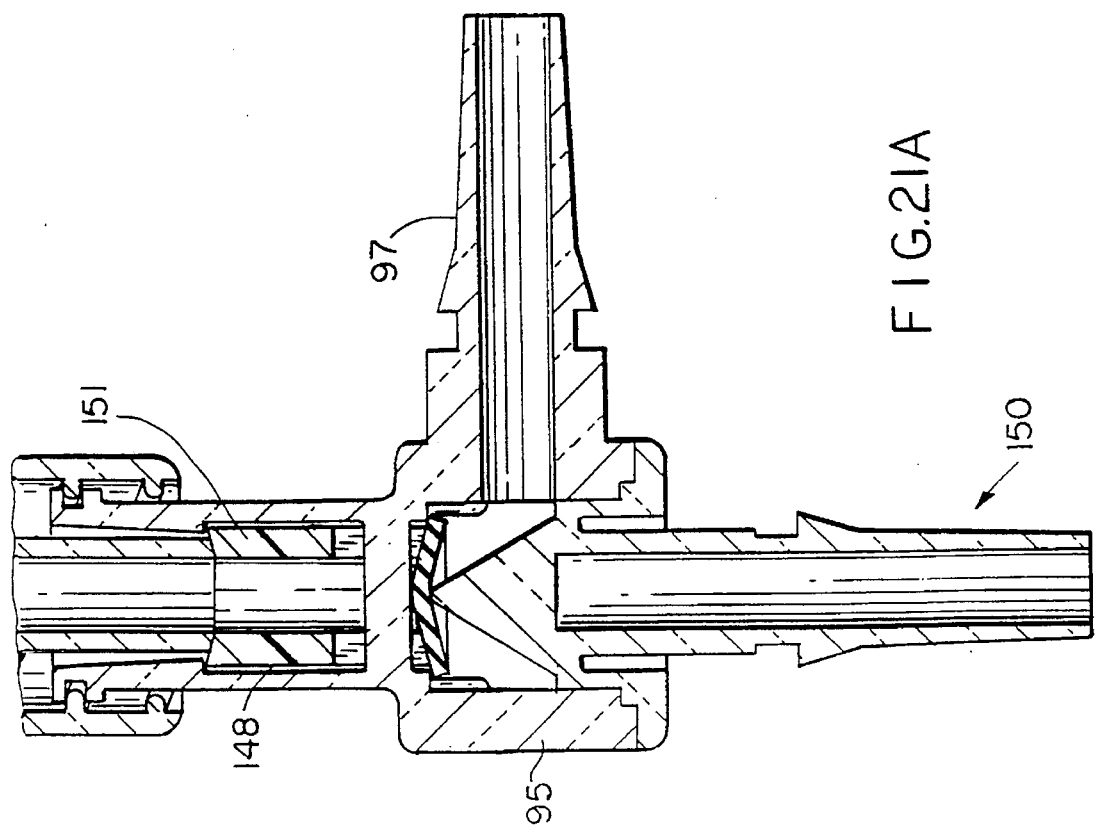

MEDICAL INFUSION DEVICES AND MEDICINE DELIVERY SYSTEMS EMPLOYING THE SAME

BACKGROUND OF THE INVENTION

1. Field of Invention

The present invention relates generally to medical infusion devices of improved construction and performance, for use in withdrawing fluids from as well as infusing fluids into an intravenous fluid stream flowing into the circulatory system of a patient, and more particularly to drug delivery systems employing the same.

2. Brief Description Of the Prior Art

In the field of modern medicine, health care practitioners utilize various types of drug delivery systems in order to safely administer medications to patients. One such drug delivery system is an IV administration system which includes a catheter, insertable to the vein of a patient, and a source of intravenous fluid connected to the catheter by way of an IV administration set with a section of flexible medical tubing. The source of intravenous fluid is typically contained within a flexible prepackaged bag suspended from a support stand positioned above the heart of the patient. The fluid is typically fed into the first primary port of the medical infusion device by way of a drip-type connector having a drip chamber and a length of plastic tubing with one-way valve. The intravenous fluid flows from the bag through the IV set and medical infusion device, along the flexible medical tubing section and into the catheter, where the intravenous fluid enters the blood stream of the patient.

In general, each prior art medical infusion device has a main housing portion with primary inlet and outlet ports, and a fluid flow passageway disposed therebetween. The function of the primary inlet and outlet ports is to permit in-line interconnection of the device within the intravenous delivery stream. The connection may be between two sections of medical tubing, between the drip-type connector and a section of medical tubing, or between the catheter and a section of medical tubing. Such connection arrangements vary depending on site of use, and patient needs.

In order that a liquid medicine may be infused into the intravenous stream and diffused therewith prior to entering the catheterized vein of the patient, prior art medical infusion devices are provided with one or more infusion ports. The actual geometrical arrangement of the infusion ports and the primary inlet and outlet ports vary from design to design. For example, see U.S. Pat. Nos. 4,666,429 (Stone); 4,908,018 (Thomsen) and 4,915,687 (Sirerr). In general, each infusion port includes a tubular section that extends from the main housing of the medical infusion device. Within the tubular section of each infusion port, there exists a check valve opening and check valve element, oftentimes realized as a resilient disc.

In a one-way check valve design, the check valve element is arranged in a normally closed configuration along its associated infusion tube. When a supply of liquid medication is injected into the infusion port by either a needleless injection syringe or medical tube delivery arrangement, a pressure-differential is created across the check valve by the incident fluid medication, causing the check valve element to reconfigure into its open configuration and thus permitting the liquid medication to flow through the check valve opening, into the intravenous stream passing through the housing of the medical infusion device, and ultimately into the circulatory system of the catheterized patient. Examples of prior art one-way check valve designs that have been connected to medical infusion devices are disclosed in U.S. Pat. No. 4,535,820.

In a two-way check valve design, a check valve is attached that permits injection and/or aspiration. Normally, the check valve is arranged in a closed configuration, preventing fluid medication to flow across the check valve opening and into the intravenous stream. When a check valve plunger is physically actuated (i.e., displaced) towards a check valve opening, the check valve element is rearranged and held in an open configuration, permitting gravity flow or two-way fluid flow across the check valve opening. The advantage of such medical infusion devices is that they can be used to inject or drip fluid medications into the primary fluid stream as well as aspirate fluids therefrom as desired or required in various patient applications. Examples of two-way check valve designs are disclosed in U.S. Pat. Nos. 4,683,916 and 5,190,067.

While most prior art medical infusion devices of the designs described above have proven useful to the medical arts, such devices have not been without significant shortcomings and drawbacks.

In particular, prior art medical infusion devices have check valve structures mounted along the tubular sections of their infusion ports. Thus, it has not been possible to infuse medications and nutrients directly into the primary intravenous stream flowing through such prior art medical infusion devices. This has resulted in a number of significant consequences. In particular, when using a needleless injection syringe to inject a dosage of medication into the infusion port of a prior art medical infusion device, a residual amount of such injected medication unavoidably resides (i.e., accumulates) along the infusion tube portions of prior art medical infusion devices, (i.e., between the check valve opening and the device housing) and never infuses into the intravenous stream. Thus, when using prior art medical infusion devices, it has been very difficult to determine whether a precisely metered dosage of injected medication is actually infused into the patient's circulatory system.

The placement of check valve structures along the infusion tube portions of prior art medical infusion devices necessitates that such infusion tubes be longer than otherwise desired. Consequently, the infusion tube portions of prior art medical infusion devices have been susceptible to fracture when connecting infusion devices to the infusion ports, due primarily to torques generated therealong during fluid infusion and aspiration operations.

Prior art medical infusion devices require the use of solvent bonding in order to securely bond check valve structures to their respective infusion ports. Consequently, this feature of prior art medical infusion devices has resulted in the undesirable leaking and cracking of check valves and the medical infusion devices within which they are installed.

The use of sonic welding or solvent bonding to connect discrete infusion tubes to the housing of prior art medical infusion devices has resulted in devices susceptible to fracture and thus fluid leakage.

In addition, the overall design and construction of prior art medical infusion devices have rendered manufacturing such devices a complicated process, thus increasing the overall cost of such medical devices.

Thus, there is a great need in the art for a medical infusion device of improved design and construction which can be used to inject as well as aspirate fluids passing through its primary fluid flow channel, while avoiding the shortcomings and drawbacks of prior art device and methodologies.

OBJECTS OF THE PRESENT INVENTION

Accordingly, it is a primary object of the present invention to provide a novel medical infusion device that can be used to inject and gravity feed, as well as aspirate fluids passing through its primary fluid flow channel, while providing for a minimum of dead-space downstream of the valve sealing element.

A further object of the present invention is to provide such a medical infusion device, in which the check valve assembly is installed within a check valve chamber integrally formed along the primary fluid flow channel of the device housing between the primary fluid inlet and outlet ports thereof.

A further object of the present invention is to provide a medicine infusion/withdrawal system using the medical infusion device of the present invention with a needleless injector syringe that permits health-care workers to inject medicines and aspirate fluids along infusion port flow channels, without the attendant risks of needle-sticking injuries and the like. A further object of the present invention is to provide a medical infusion device which eliminates the need to solvently bond check valve structures to respective infusion ports, and thus effectively reduce undesirable leaking and cracking of valves and housings.

A further object of the present invention is to provide a medical infusion device having a one-way check valve integrally formed within a check valve chamber disposed along its primary fluid flow channel formed through its housing.

A further object of the present invention is to provide a medical infusion device having a two-way check valve integrally formed within a check valve chamber disposed along its primary fluid flow channel formed through its housing.

A further object of the present invention is to provide such a medical infusion device, which permits the use of infusion tubes at each infusion port, thereby decreasing the possibility of accidentally fracturing the device housing due to substantial torques imposed thereupon during normal infusion and aspiration operations performed using the medical infusion device.

A further object of the present invention is to provide a medical infusion device having a primary flow channel geometry through each check valve chamber that optimally minimizes primary fluid flow obstruction, while maximizing infusion fluid flow and mixing within the primary intravenous fluid flowing through the primary fluid flow channel of the medical infusion device.

A further object of the present invention is to provide such a medical infusion device, in which the geometrical arrangement of the infusion port(s) and the primary fluid inlet and outlet ports may be arbitrarily selected.

A further object of the present invention is to reduce the number of parts in medical infusion devices.

A further object of the present invention is to provide such a medical infusion device that reliably seals the primary flow channel off from the infusion ports, except for when its mated needleless injection syringe is connected to its infusion port and the syringe connector thereof is deliberately rotated by a predetermined amount in order to actuate the flexible check valve disc in its check valve chamber.

A further object of the present invention is to provide a multi-port medical infusion device that is easy to manufacture by hand or robotic manufacturing technology.

A further object of the present invention is to provide a novel medical infusion device having a design and construction which reduces manufacturing costs and assembly time.

Yet an even further object of the present invention is to provide a medicine delivery system employing a medical infusion device having the structural and functional features described above.

Further objects of the present invention will be apparent hereinafter and in the claims to invention.

SUMMARY OF THE INVENTION

In general, the medical infusion device of the present invention includes at least one check valve chamber through which a primary intravenous stream is arranged to pass by way of a primary fluid inlet port and a primary outlet port. Each check valve chamber has at least one physically associated infusion port through which a medicational or nutritional fluid can be injected in any number of possible ways. Each check valve chamber has an interior volume, a check valve opening formed between its interior volume and its associated infusion port, a check valve chamber opening formed through the check valve chamber and axially aligned with the check valve opening, a flexible check valve element, and a check valve support element. The check valve support element is installed through the check valve chamber opening and is mounted within the check valve chamber so as to support the flexible check valve element over the check valve opening in a normally closed configuration, and thus prevents fluid from passing therethrough. By virtue of this novel construction, medicational or nutritional fluids can now, be easily injected into the infusion port of the medical infusion device and directly infused into the primary intravenous stream flowing through its check valve chamber with minimal loss of injected fluid.

By departing from conventional principles and designs, the medical infusion device of the present invention effectively solves the numerous problems associated with prior art medical infusion devices and systems. In addition, when practicing the various illustrative embodiments of the present invention disclosed herein, significant advantages in performance and/or manufacturing can be acquired.

BRIEF DESCRIPTION OF THE DRAWINGS

For a more complete understanding of the Objects of the Present Invention, the following Detailed Description of the Illustrative Embodiments should be read in conjunction with the following Drawings, wherein:

FIG. 3 is an exploded, perspective partially fragmented view of the medical infusion device of the first illustrative embodiment, showing the protective infusion port cap, the infusion tube portion and check valve chamber of the housing, the flexible check-valve disc, the check valve plunger, and the check valve support structure.

FIG. 4 is a cross-sectional view, taken along line 4—4 in FIG. 3, showing the check valve opening and its transverse support element bisecting the same, as well as the interior volume of the check valve chamber of the first illustrative embodiment;

FIG. 5 is a plan view of the check valve support structure of the first illustrative embodiment, shown removed from the check valve chamber of the medical infusion device thereof;

FIG. 6 is a first elevated side view of the check valve support structure of FIG. 3, removed from the medical infusion device of the first illustrative embodiment, and showing the side of the check valve support projection thereof;

FIG. 7 is a second elevated side view of the check valve support structure of FIG. 3, removed from the medical infusion device of the first illustrative embodiment, and showing the end of the check valve support projection thereof;

FIG. 18 is an exploded, perspective partially fragmented view of the single-port, T-type, medical infusion device of the third illustrative embodiment of the present invention, showing the protective infusion port cap, the infusion port and check valve chamber, the flexible check valve disc, the check valve plunger, and the check valve support structure thereof;

FIG. 19A is a cross-sectional view of the single-port Y-type medical infusion device of the second illustrative embodiment, showing the needleless injection syringe connector connected to the infusion port thereof with its actuator portion positioned relative to the check valve plunger so that the flexible check valve is arranged in its normally closed configuration;

FIG. 19B is a cross-sectional view of the single-port Y-type medical infusion device of the second illustrative embodiment, showing a needleless injection syringe connector connected to the infusion port thereof with its actuator portion engaging and displacing the check valve plunger so that the flexible check valve disc is arranged in its open configuration;

FIG. 21A is a cross-sectional view of the single-port T-type medical infusion device of FIG. 20, showing a needleless injection syringe connector connected to the infusion port thereof with its actuator portion positioned relative to the check valve plunger so that the flexible check valve disc is arranged in its normally closed configuration; and FIG. 21B is a cross-sectional view of the single-port T-type medical infusion device of FIG. 20, showing the needleless injection syringe connector connected to the infusion port thereof with its actuator portion engaging and displacing the valve plunger so that the flexible check valve disc is arranged in its open configuration.

DETAILED DESCRIPTION OF ILLUSTRATIVE EMBODIMENTS

Figure 1:
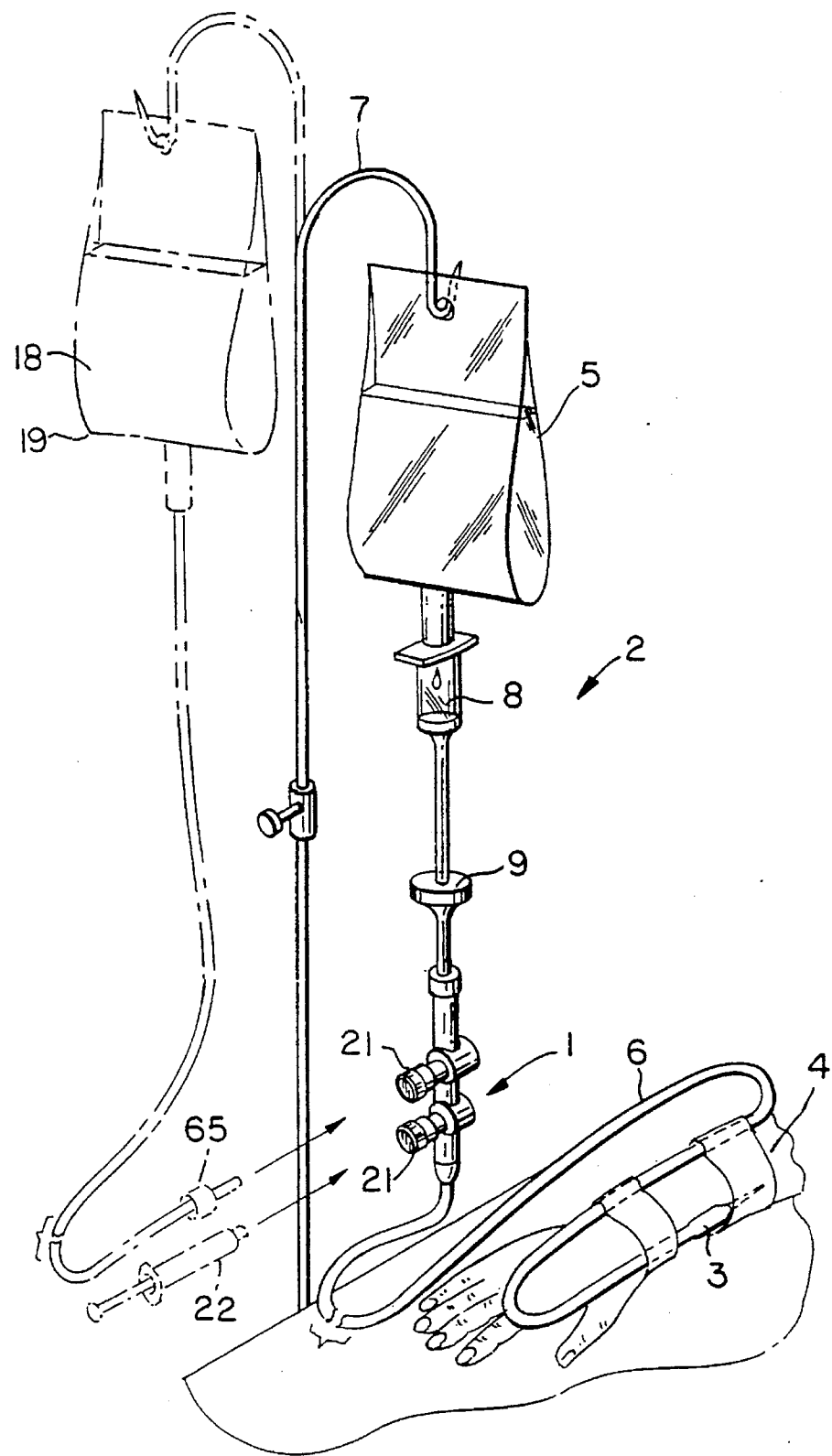
FIG. 1 is a perspective view of an intravenous type drug delivery system, in which a dual-port medical infusion device of the present invention is connected between a catheter and a drip-type fluid connector.

Referring now to the figures in the accompanying Drawings described above, a detailed description of the illustrative embodiments of the present invention is provided below. Throughout the various drawings, like structures will be indicated by like reference numerals.

In FIG. 1, a typical environment is illustrated for any one of the medical infusion devices of the present invention. In the figure drawing of FIG. 1, the multi-port medical infusion device 1 of the first illustrative embodiment is shown used in a conventional intravenous delivery (e.g., medicine or nutrient infusion) system 2. As shown, the system 2 comprises a catheter 3 insertable to the vein of a patient 4, and a source of intravenous fluid 5 connected to the catheter by way of multi-port medical infusion device 1 and a section of flexible medical tubing 6. In the system of FIG. 1, the source of intravenous fluid 5 is contained within a flexible prepackaged bag that is suspended from a support stand 7 above the heart of the patient, and connected to multi-port medical infusion device 1 by way of a conventional drip-connector 8 and one way check valve 9.

Figure 2A:
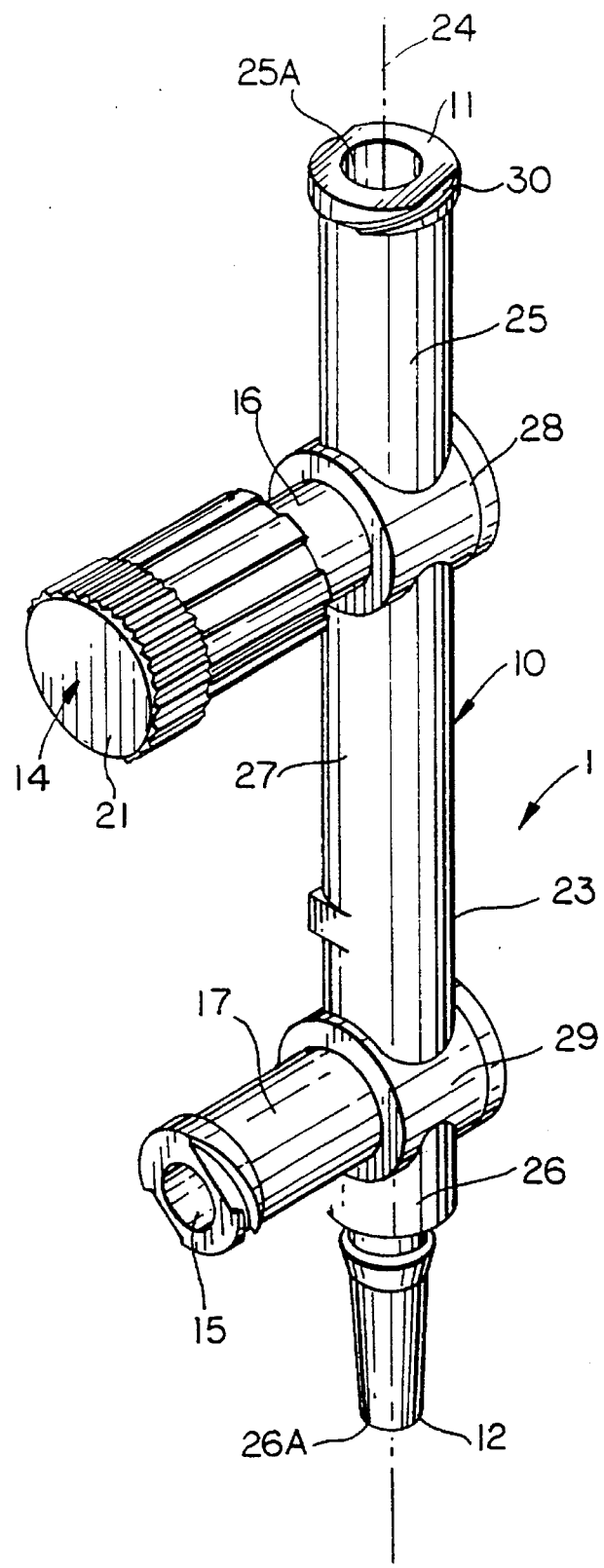
FIG. 2A is a perspective view of the dual-port medical infusion device of FIG. 1, showing a protective cap connected to the first infusion port of the multi-port medical infusion device, while the protective infusion port cap is removed from the second infusion port for connecting a needleless injection syringe or a flexible medical infusion/aspiration tube.
Figure 8:
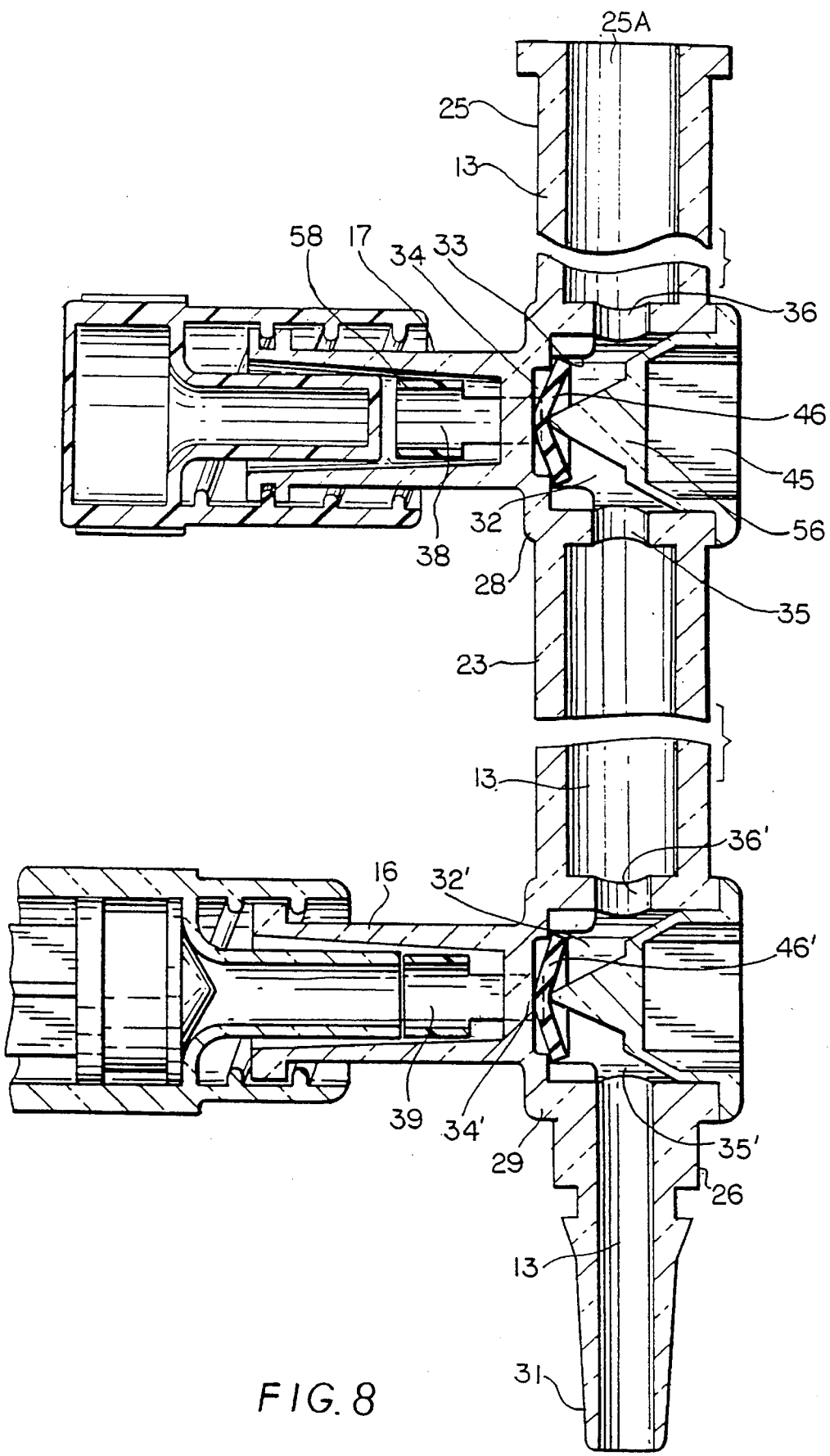
FIG. 8 is a longitudinal cross-sectional view of the medical infusion device of the first illustrative embodiment, showing the primary fluid inlet and outlet ports, the first and second check valve chambers operably associated therewith, the first and second infusion ports operably connected to a medical infusion tube connector and a needleless syringe connector, respectively, first and second flexible check valve discs each in a normally closed configuration and supported by first and second check valve support structures.

As best shown in FIG. 2A and 8, multi-port medical infusion device 1 has a main housing portion 10 with primary fluid inlet and outlet ports 11 and 12 respectively, and a fluid flow passageway (i.e., channel) 13 disposed therebetween. The function of the primary fluid inlet and outlet ports 11 and 12 is to permit in-line interconnection of the device within the intravenous delivery stream. In general, the connection may be between two sections of medical tubing, between the drip-type connector 8 and a section of medical tubing, or between the catheter and a section of medical tubing. In the illustrative embodiment of FIG. 1, primary fluid inlet and outlet ports 11 and 12 are connected to drip connector 8 and medical tubing section 6, respectively, as shown.

As shown in FIG. 2A, medical infusion device 1 includes first and second infusion ports 14 (hidden by protective cap 21) and 15, respectively, for directly infusing a liquid medicine into the intravenous stream prior to entering the catheterized vein of the patient. In general, the actual geometrical arrangement of the infusion ports and the primary fluid inlet and outlet ports will vary from embodiment to embodiment of the present invention. As shown, infusion ports 14 and 15 include tubular sections 16 and 17 (i.e., infusion tube portion) respectively which extend from the main housing.

As illustrated in FIG. 1, in particular, a source of medication 18, contained in a flexible bag 19 supported from stand 7, may be releasibly connected to the first infusion port 14. The purpose of this arrangement is to directly infuse the liquid mediation or nutrient into the intravenous stream passing from the primary fluid inlet port 11 to the primary fluid outlet port 12 of the medical infusion device. To achieve the necessary connection with the first infusion port, the protective infusion port cap 21, preferably supplied with each infusion port, is removed. The height of the flexible bag 19 on stand 7 will cause a pressure head which will permit flow of medication 18 through infusion port 14 into fluid passageway 13.

Figure 2B:
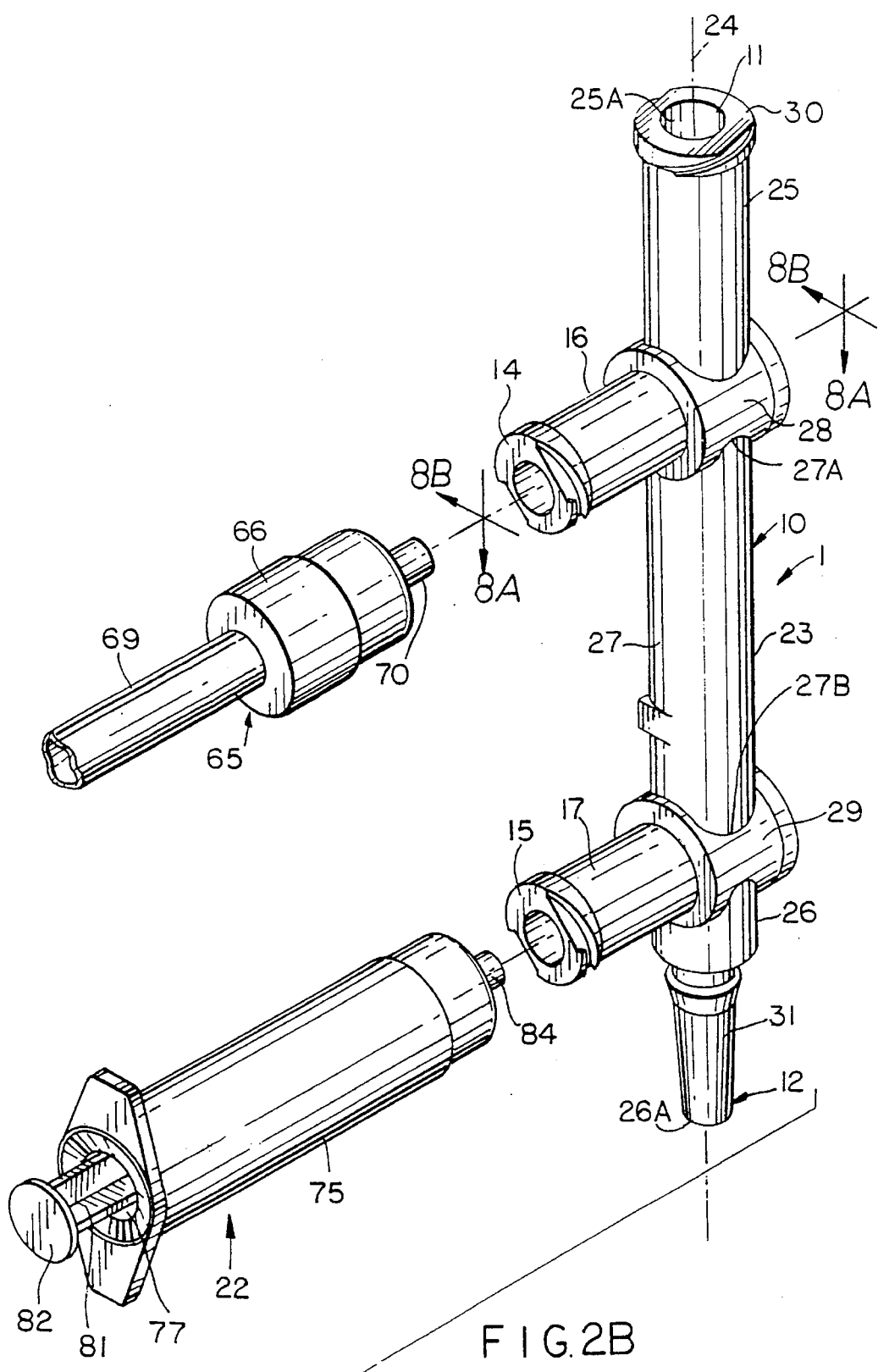
FIG. 2B is a perspective view of the dual-port medical infusion device of FIG. 1, showing a medical infusion tube being connected to the first medical infusion port of the multi-port medical infusion device of the first illustrative embodiment, while a needleless injection syringe is being connected to the second infusion port.
Figure 2C:
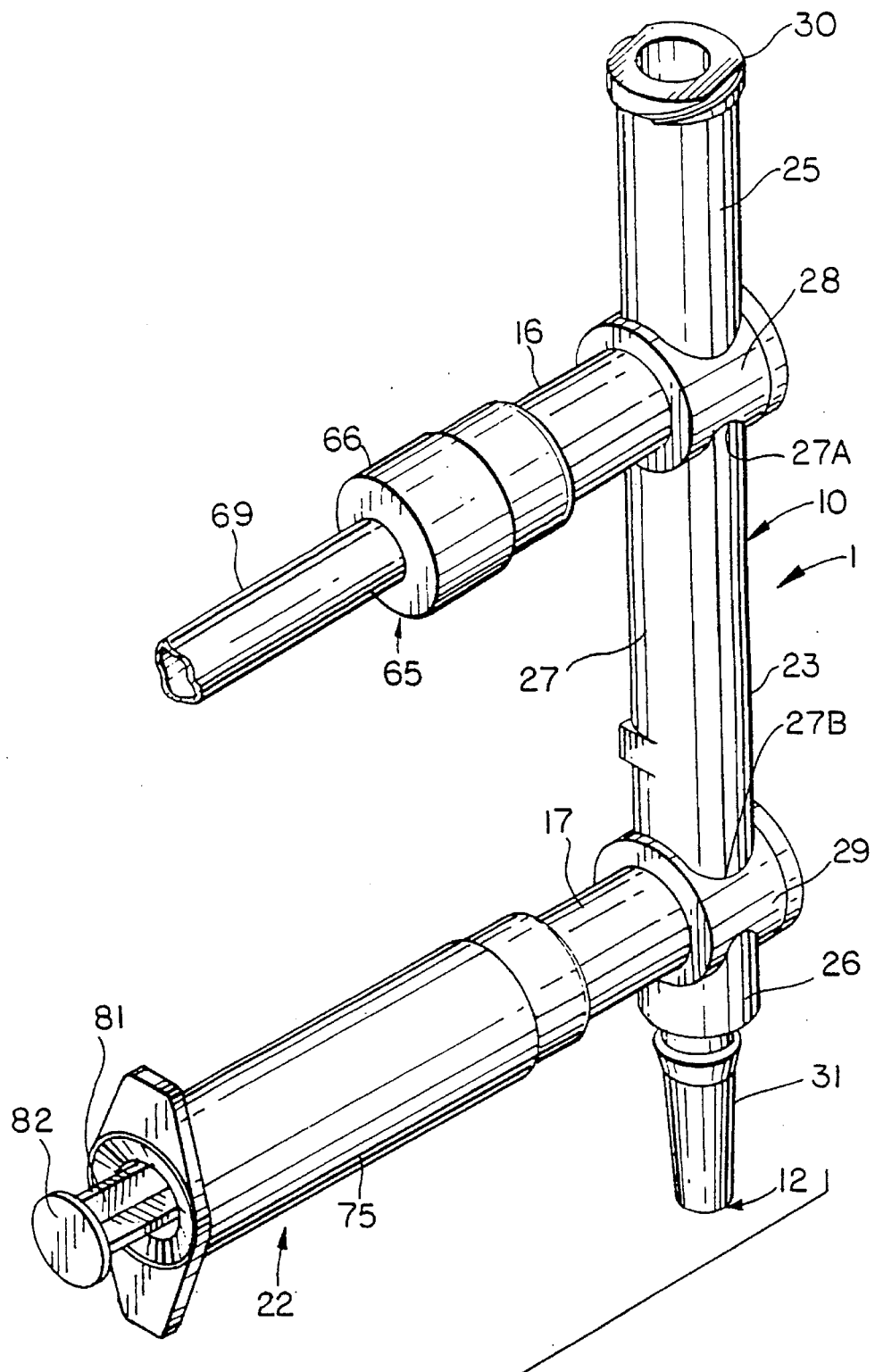
FIG. 2C is a perspective view of the dual-port medical infusion device of FIG. 1, showing a medical infusion tube connected to the first medical infusion port of the multi-port medical infusion device of the first illustrative embodiment, while a needleless injection syringe is connected to the second infusion port.
Figure 10A:
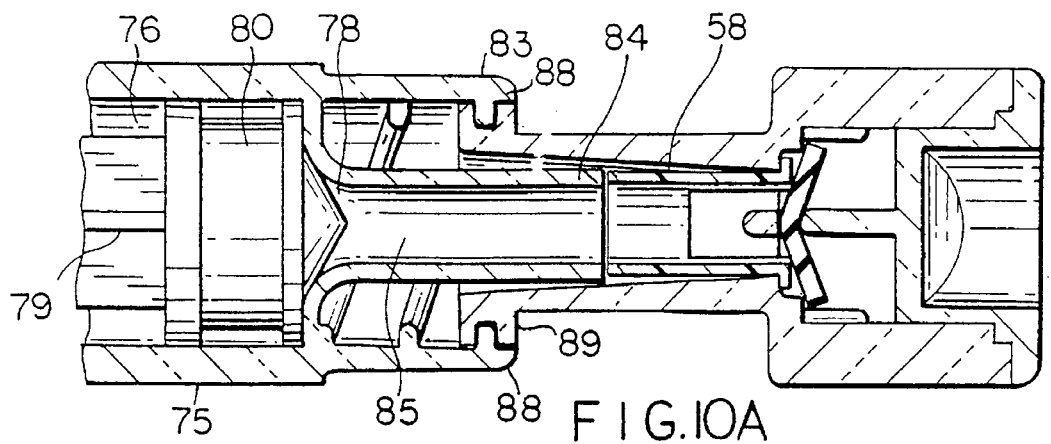
FIG. 10A is a cross-sectional view of the dual-port medical infusion device of the first illustrative embodiment, taken along line 9B—9B of FIG. 2C, showing an injection syringe connector connected to the second infusion port with its actuator portion disengaged from the check valve plunger thereof so that the flexible check valve disc is arranged in its normally closed configuration.

While not visible in the views shown in FIGS. 1, 2A or 2B, a plunger-actuatable check valve mechanism is associated with each infusion port 14, 15 of the first illustrative embodiment. Each such check valve mechanism is embodied within its respective check valve chamber, and is normally closed in order to prevent medical fluid infusion into the primary fluid stream. In this particular illustrative embodiment of the present invention, the check valve mechanism must be actuated by a check valve plunger installed along the infusion port in order to permit either infusion of fluid into or withdrawal of fluid samples from its associated infusion port. In other embodiments of the present invention, such as shown in FIGS. 10D–10F, a fluid pressure-actuated check valve mechanism is embodied with the check valve chamber associated with each infusion port. Rather than using a check valve plunger or like structure, the fluid pressure created by an injected medical fluid actuates the check valve mechanism permitting one-way fluid infusion into the primary intravenous fluid stream. The details of such plunger-actuated and pressure-actuated operations will be described in great detail hereinafter.

As shown in FIGS. 1 and 2B, a second source of medication contained within needleless injection syringe 22 may be directly infused into the primary intravenous fluid stream by way of the second infusion port 15. Alternatively, if the first infusion port 14 is not being used, needless-injection syringe 22 may use the first infusion port to infuse medication directly into the primary intravenous stream. In either case, the first and second infusion ports may be used interchangeably. The manner in which needleless injection syringe 22 is releasibly connected to its selected infusion port will be described in greater detail hereinafter.

While the figure drawings of FIGS. 2A and 2B show various types of medication sources that may be releasibly connected to the infusion ports of the infusion devices of the present invention, it is understood, however, that there will be other types of medication sources and connectors associated therewith that may be directly or indirectly connected to the infusion ports of such medical infusion devices. Typically, when a medical infusion device of the present invention is removed from its sterilized package, the inlet opening at the end of each infusion port formed thereon will be closed off by protective infusion port cap 21 connected over the end-opening provided at the distal portion of its infusion port. When the protective infusion port cap is screwed onto its infusion port, it does not cooperate with the check valve mechanism associated with the infusion port and thus does not actuate the same. This feature of the present invention will be described in greater detail hereinafter with reference to FIGS. 8 and 8C.

As shown in FIGS. 2A and 2B, multi-port infusion device 1 comprises a single piece (i.e., unitary) housing in the shape of a manifold structure. As shown, the manifold structure has an elongated tube 23 which extends along a central longitudinal axis 24 passing through the housing. As shown, the elongated tube 23 comprises a number of structural features, namely: a primary fluid inlet tube portion 25 having a primary fluid inlet tube portion 25A; a primary fluid outlet tube portion 26 having a primary fluid outlet tube portion 26A; a central tube portion 27; a primary fluid passageway (i.e., channel) 13 (FIG. 8); a first check valve chamber 28; a second check valve chamber 29; and first and second infusion tube portions 16 and 17, respectively. The primary fluid inlet tube portion 25 is connectable to a first flexible tubing section or drip connector 8, as shown in FIG. 1 by way of threaded connector flange 30, and shall be referred to as the primary fluid inlet port of the medical infusion device. Similarly, the primary fluid outlet portion 26 is connectable to a second tubing section or other type of connector, as shown in FIG. 1 by way of tapered tube connector 31, and shall be referred to as the primary fluid outlet port of the medical infusion device. The relative location of the primary fluid inlet and outlet ports is not critical to the practice of the principles of the present invention.

As shown in FIGS. 2A and 2B, the central tube portion 27 has first and second end portions 27A and 27B, respectively. The first chamber 28 is disposed between primary fluid inlet tube portion 25 and the first end portion of the central portion 27A. In a symmetric manner, the second chamber 29 is disposed between primary fluid outlet tube portion 26 and the second end portion of the central portion 27B. As shown in FIG. 8, primary fluid passageway 13 continuously extends from primary fluid inlet port 11 to primary fluid outlet port 12 and passes through first check valve chamber 28, central tube portion 23 and second check valve chamber 29.

As best shown in FIGS. 4 and 8, 8A and 8B, the first check valve chamber has an interior volume 32 surrounded by an interior wall surface 33 defined by a truncated cylindrical geometry and having planar side wall surface portions 51 and 52; a first check valve opening 34 formed in the upper portion of the first check valve chamber; a first pair of side wall openings 35 and 36 formed through the side wall surfaces of the first check valve chamber; and a first check valve chamber opening 37 axially aligned with the first check valve opening 34. Likewise, the second check valve chamber has an interior volume 32' surrounded by an interior wall surface 33' defined by a truncated cylindrical geometry; a second check valve opening 34' formed in the upper portion of the second check valve chamber; a second pair of opposing side wall openings 35' and 36' formed through the side wall surfaces of the first check valve chamber; and a second check valve chamber opening 37' axially aligned with the second check valve opening 34'.

As shown in FIGS. 4, 8, 8A and 8B, first check valve chamber opening 34 leads into the interior volume 32 of the first check valve chamber, whereas second check valve chamber opening 34' leads into the interior volume 32' of the second check valve chamber. The first pair of opposing side wall openings 35 and 36 lead into the flow conduits of tube portions 25 and 23, respectively, whereas the second pair of opposing side wall openings 35' and 36' lead into the flow conduits of tube portions 26 and 23, respectively . Also shown, first check valve opening 34 leads into the interior volume 38 of the first infusion tube portion 16, whereas second check valve opening 34' leads into the interior volume 39 of the second infusion tube portion 17. Notably, each check valve opening is disposed at the interface between the interior volume of the check valve chamber and the interior volume of its associated cylindrical tube portion. As will be described in greater detail hereinafter, it is across the check valve opening without its associated check valve housing, that liquid medications, nutrients or the like are infused into the primary intravenous stream flowing along the primary fluid channel of the device.

Figure 8A:
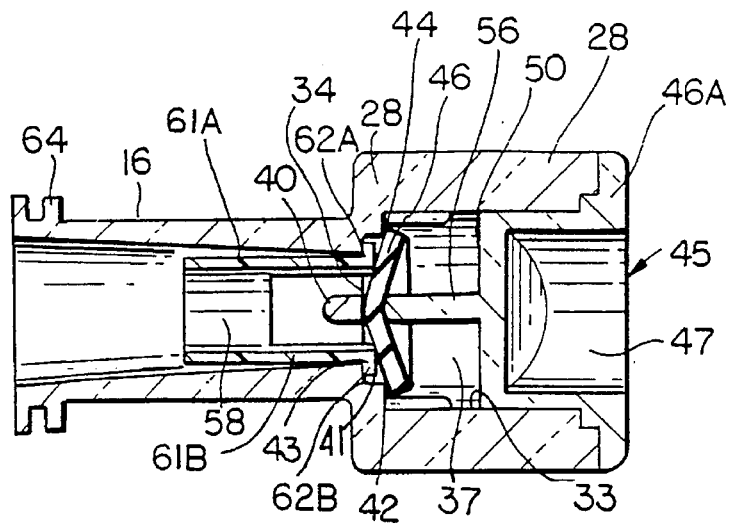
FIG. 8A is a cross-sectional view of the dual-port medical infusion device of the first illustrative embodiment, taken along line 8A—8A of FIG. 2B, showing the flexible check valve disc arranged in its normally closed configuration.

As shown in FIGS. 4 and 8A, each check valve opening in the illustrative embodiments has a substantially circular geometry and is bisected by an optional check valve bar element 40. When included in the overall structure, this element helps prevent blowout of the check valve disc 46 through infusion tube position 16. As shown, check valve support element 40 has a thin widthwise dimension, is disposed within the plane of the check valve opening, and is perpendicular to its associated transverse axis. As illustrated in FIGS. 8 and 8A, first and second annular recesses 41 and 42 are formed at the check valve interface, immediately adjacent each check valve opening below the upper portion of the check valve chamber. As shown in FIG. 8A, first annular recess 41 is spaced apart from second annular recess 42. Associated with first and second annular recesses 41 and 42 are first and second annular support surfaces 43 and 44, respectively. The first annular support surface 43 is adjacent the end of cylindrical interior volume of the infusion tube, whereas the second annular surface 44 is disposed adjacent the upper portion of the interior volume of the check valve chamber.

As shown in FIGS. 5–7 and 8A, each infusion port also has an associated check valve support structure 45 for supporting a flexible check valve disc 46 against second annular support surface 44 and against optional check valve bar element 40. The contact between check valve support structure 45, in particular point 56 and check valve disc 46 creates an annular seal between disc 46 and support surface 44 to close off associated check valve opening 34. In the illustrative embodiments disclosed herein, each flexible check valve disc is preferably made from silicone rubber or functionally equivalent material. The manner in which the flexible check valve disc is reconfigured during its closed and open configurations, will be described in greater detail hereinafter.

As shown in FIGS. 5–7, each check valve support structure 45 has a number of structural features, namely: a truncated cylindrical base portion 46A having a hollow interior 47; an annulus-shaped cover flange 48 extending outwardly from the bottom portion of truncated cylindrical base portion 46A; a pair of planar side surfaces 49 and 50, for engaging planar side wall surfaces 51 and 52, respectively; a planar top fluid-flow surface 53, extending within a plane disposed substantially parallel to annulus-shaped cover flange 48; and a pair of planar side fluid-flow surfaces 54 and 55 disposed at about 45 degrees from the plane with which planar top fluid-flow surface 53 extends. Notably, the outer dimensions of the truncated cylindrical base 46A are slightly less than the interior dimensions of the truncated cylindrical interior volume of the associated check valve chamber.

As shown in FIGS. 5–7, each check valve support structure 45 also includes a check valve support element 56 which, in the illustrative embodiments, has a triangular-shaped geometry and a thin width dimension along its longitudinal extent. When check valve support structure 45 is installed within its associated check valve chamber, the thin width dimension of check valve support element 56 minimizes the obstruction of fluid flow along its longitudinal extent. Although valve support element 56 has a thin triangular shape, other known shapes can be used. It is important to use a shape that minimizes fluid interference within check valve chambers 28 and 29 and overall fluid passageway 13.

One way to ensure proper alignment of the support 56 is shown in FIGS. 5–7, 8A and 8B, the planar side fluid-flow surfaces 54 and 55 on truncated cylindrical base portion 46A register and engage with side wall surfaces 51 and of 52 of the check valve chamber. As shown in these figures, this registration (i.e., alignment) mechanism ensures that when the check valve support structure 45 is installed within its associated check valve chamber, the thin check valve support element 56 is always aligned (i.e., registered) with the its thinner width dimension (shown in FIG. 7 and 8A) in planar with the flow in passageway 13. Similarly, the wider dimension of support element 56 (FIGS. 6 and 8B) is parallel to the fluid flow. At the same time, the check valve chamber opening 37 is closed off by the hollow, truncated cylindrical base portion 46A, and thus functions as a chamber opening cover.

As shown in FIGS. 3, 8 and 8A, a check valve plunger 58 is installed within the interior volume of its associated cylindrical infusion tube during manufacture of the medical infusion device. In this illustrative embodiment of the multi-port medical infusion device, each check valve plunger 58 is realized as a cylindrical tube 59 having a pair of diametrically opposing side wall cut-out portions 60A and 60B. As shown, these side wall cut-out portions are laterally separated by two thin diametrically opposed wall portions 61A and 61B, which extend along the longitudinal extent of the check valve plunger. As shown in these figures, these wall portions 61A and 61B terminate in transverse projections 62A and 62B, which extend radially outward from each other in a direction substantially perpendicular to the longitudinal axis of cylindrical tube 59. When slid along its associated infusion tube, wall portions 61A and 61B retract inwardly until the projections 62A and 62B reach and snap into first annular recess 41. Plunger 58 is illustrative of a number of known check valve plunger designs. Similarly, the check valve plunger and check valve disc may be a unitary structure. Such a device would similarly be held open by an actuator and would seal in a normally closed configuration.

Figure 8B:
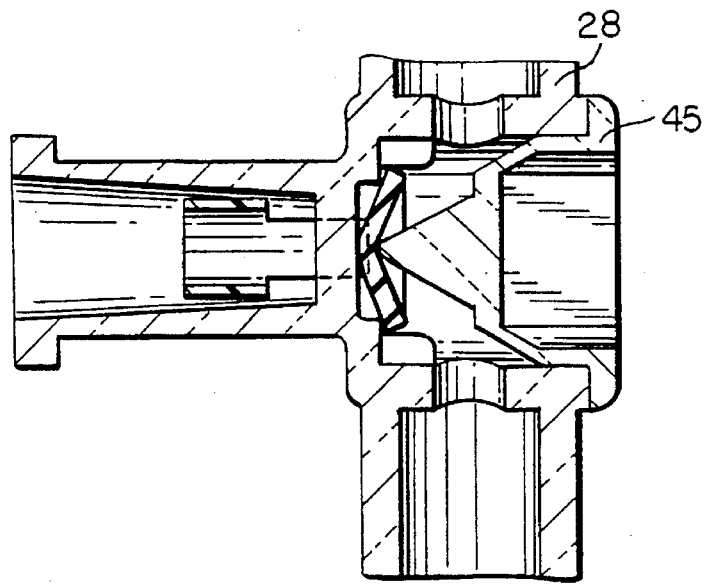
FIG. 8B is a cross-sectional view of the dual-port medical infusion device of the first illustrative embodiment, taken along line 8B—8B of FIG. 2B, showing the flexible check valve disc arranged in its normally closed configuration.
Figure 8C:
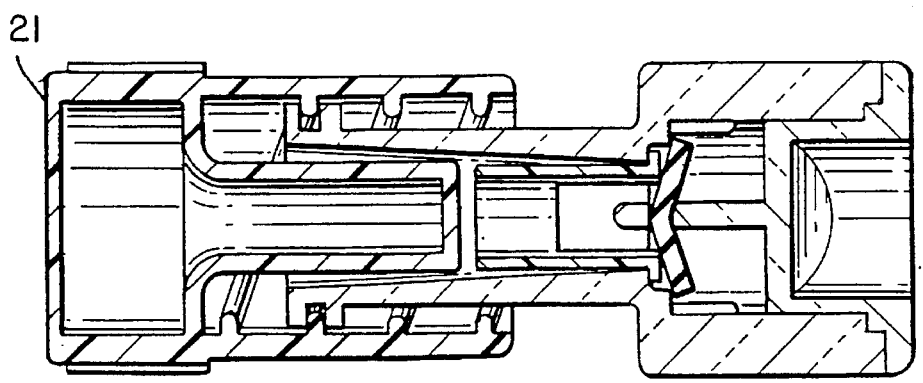
FIG. 8C is a cross-sectional view of the dual-port medical infusion device of the first illustrative embodiment, taken along line 8C—8C of FIG. 2A, showing the protective infusion port cap connected to the first infusion port, with the flexible check valve disc arranged in its normally closed configuration.

When the check valve components are completely assembled in the manner shown in FIG. 3, the bottom surface of flexible check valve disc 46 engages point 56 which facilitates the upper surface of flexible check valve disc 46 to engage second annular surface 44 and effect an annular seal therebetween. At the same time, if the valve bar element 40 is incorporated for blow back protection, the central portion of the upper surface of the check valve disc will be in contact with the bottom surface of bar element 40. As described, the flexible check valve disc is deemed to be in its normally closed configuration, as shown in FIGS. 8A–8C.

As shown in FIG. 8A, each infusion tube bears exteriorly disposed coupling threads 64 formed on the outer end portion of each infusion tube 16, 17. These exterior coupling threads permit easily connection of the infusion port to either the connector portion of an infusion tube connector 65 shown in FIGS. 9A–9C, or to the connector portion of needleless injection syringe 22 shown in FIGS. 10A–10C.

Figure 9A:
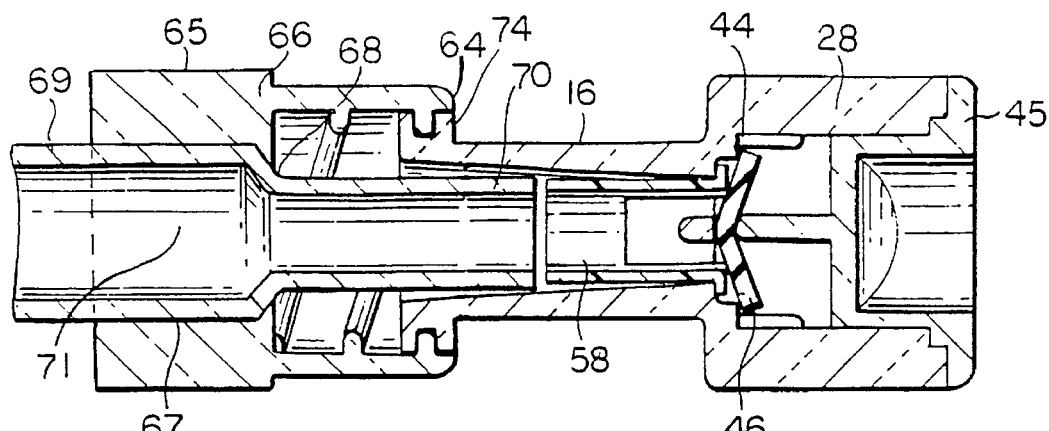
FIG. 9A is a cross-sectional view of the dual-port medical infusion device of the present invention, taken along line 9A—9A of FIG. 2C, showing medical infusion tube connected to the first infusion port with its actuator portion positioned relative to the check valve plunger thereof so that the flexible check valve disc is arranged in its normally closed configuration.
Figure 9B:
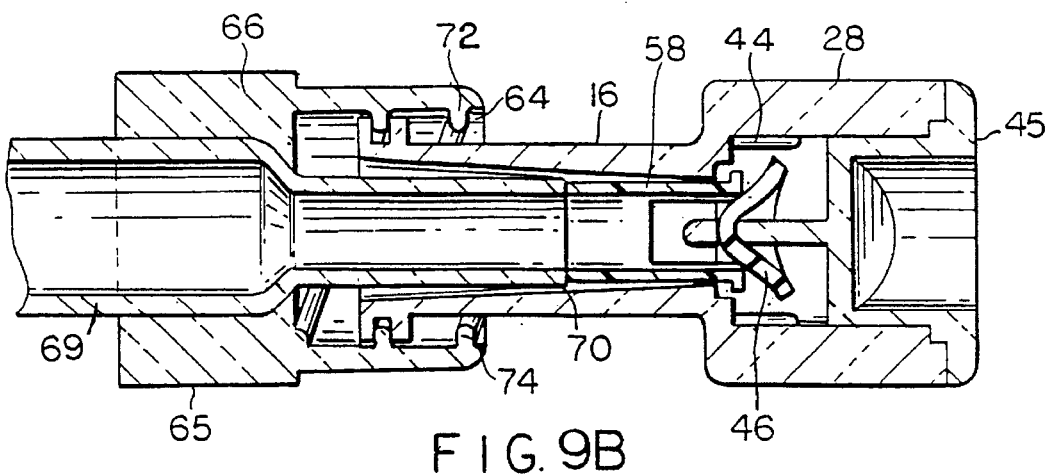
FIG. 9B is a cross-sectional view of the dual-port medical infusion device of the first illustrative embodiment, taken along line 9A—9A of FIG. 2C, showing a medical infusion tube connector connected to the first infusion port with its actuator portion engaging and displacing the check valve plunger thereof so that the flexible check valve disc is arranged in its open configuration.
Figure 9C:
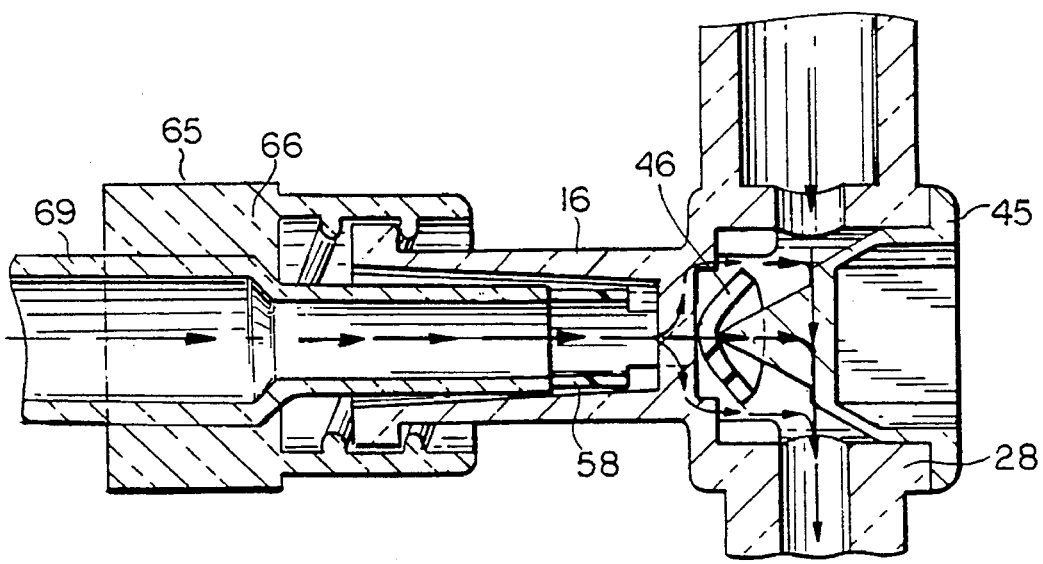
FIG. 9C is a cross-sectional view of the dual-port medical infusion device of the first illustrative embodiment, taken along line 9C—9C of FIG. 2C, showing a medical infusion tube connector connected to the first infusion port with its actuator portion engaging and displacing the check valve plunger thereof so that the flexible check valve disc is arranged in its open configuration, so that fluid can be infused into the primary intravenous stream.

As shown in FIGS. 9A–9C, infusion tube connector 65 has a body portion 66 of substantially symmetrical geometry. Within the connector body portion 66, a tube receiving bore 67 is formed, tapering down in diameter towards the mid-section 68 of the connector body portion. As shown, this permits the end portion of a section of the flexible medical tubing 69 to be press-fitted into the tube receiving bore 67 in a secure manner. Alternatively, adhesives or sonic welding may be used to effect bonding between the tubing and the receiving bore within the connector body portion of infusion tube connector 65.

As shown in FIGS. 9A–9C, the tapered bore 67 continuously extends into a cylindrically-shaped actuator portion 70. The actuator portion 70 has a flow channel 71 in fluid communication with the end of the secured section of flexible medical tubing 69. The outer diameter of actuator portion 70 is slightly less than the inner diameter of the cylindrical infusion tube portion 16 of the medical infusion device. Within the interior portion of the connector body portion 66, a set of interior screw threads 72 are formed. These threads are matched to the exterior threads 64 formed on the end of each cylindrical infusion tube portion of the medical infusion device.

In the illustrative embodiment shown in FIG. 9A, the actuator portion 70 of the medical tubing connector extends beyond the end of connector body portion 66. When the actuator portion is slid into the interior volume of infusion tube portion 16 and the interior threads 72 rotated over exterior threads 64 until the end of the actuator portion almost engages, but does not displace the check valve plunger 58. In this state, the flexible check valve disc 46 is still in its normally closed configuration. In this configuration, the interior volume within the infusion tube portion 16 is not in fluid communication with the interior volume within its associated check valve chamber, and thus fluid infusion is not possible.

As shown in FIG. 9B, by completely rotating the tubing connector body portion 66 about the end of the infusion tube portion, past lower edge 74, the actuator portion of the tubing connector is displaced along the interior volume of the infusion tube portion of the device until it engages and displaces the check valve plunger 58. The projections 62A and 62B on the end of the check valve plunger 58 reconfigure (i.e., rearrange) the resilient check valve disc 46 into its open configuration, as shown in FIG. 9B. In this configuration, the outer edge portions of the flexible check valve disc are pushed away from second annular surface 44, thus permitting fluid to flow. The valve is now in an open configuration permitting two-way flow. Assuming there is sufficient head or pressure, there will be flow from the interior volume within the infusion tube portion into the interior volume of its associated check valve chamber, as best illustrated in FIG. 9C. Notably, in this open configuration, fluid from connected infusion tubing 69 fills the interior volume of the infusion tube portion of the device, and is permitted to flow through check valve opening 34.

As the fluid flows through the check valve opening 34, it enters its associated check valve chamber and mixes with the primary intravenous fluid stream flowing along the primary flow channel 13 of the infusion device. As the infused fluid enters the check valve chamber on opposite sides of the thin check valve support element 56, minimal obstruction to infused fluid flow occurs as it enters the rapidly flowing primary fluid stream. The planar side fluid-flow surfaces 54 and 55 facilitate rapid mixing of the infused fluid into the primary fluid stream.

The present device is designed to work with all standard needleless syringes that comply with American National Standard for Luer Taper fittings ANSI/HIMA MD70.1-1983. By way of example, FIGS. 2B and 10A–10C show an illustration, needleless injection syringe 22 for use with the medical infusion device 22 comprises an assemblage of components, namely: a syringe barrel 75 having a hollow fluid cylinder 76; syringe opening 77; fluid ejection opening 78; syringe plunger 79 having a longitudinal extent, a rubber piston portion 80, plunger body portion 81 and a handle portion 82; luer lock 83; and luer tapered tip portion 84 having a fluid flow channel 85 in fluid communication with ejection opening 78. As shown in FIGS. 2B and 10A, the hollow fluid cylinder 76 formed in the syringe barrel is capable of storing a predetermined volume of medication, nutrient or the like. The syringe opening 81 in the syringe tube permits insertion of the syringe plunger 79 into the hollow fluid storage chamber. Fluid ejection opening 78 is formed in the opposite end of the syringe tube. The function of ejection opening 78 is to allow the medication or nutrient fluid to be ejected through ejection opening 78 and into fluid flow channel 85 of the actuator portion when the handle portion 82 is depressed into the hollow fluid cylinder 76.

As best shown in FIG. 10A, luer lock 83 extends from the end of the syringe tube 75 adjacent its ejection opening 78. As shown, actuator portion 84 is realized as a hollow tube extending from the ejection opening along the longitudinal extent of the syringe. The outer diameter of the actuator portion is slightly less than the inner diameter of the each infusion tube 16, 17. This permits the actuator portion 84 to slide along the interior volume thereof, engage the check valve plunger 58 within the infusion tube, and thus actuate the flexible check valve disc 46.

As shown in FIG. 10A, a set of interior screw threads 87 are formed within the interior portion of the connector body portion. These threads are matched to the exterior threads formed on the end of each infusion tube portion of the medical infusion tube. As shown, actuator portion 84 of the syringe connector extends beyond the end of connector body portion 83. When the actuator portion 84 is slid into the infusion tube and interior threads 87 are rotated over exterior threads 64 until the end of the actuator portion 84 almost engages the end of the check valve plunger 58, the check valve plunger is not physically displaced, thus leaving the flexible check valve disc 46 in its normally closed configuration. In such a configuration, the interior volume within the infusion tube portion is not in fluid communication with the interior volume within its associated check valve chamber, and thus fluid infusion into the check valve chamber is not possible in this configuration.

Figure 10B:
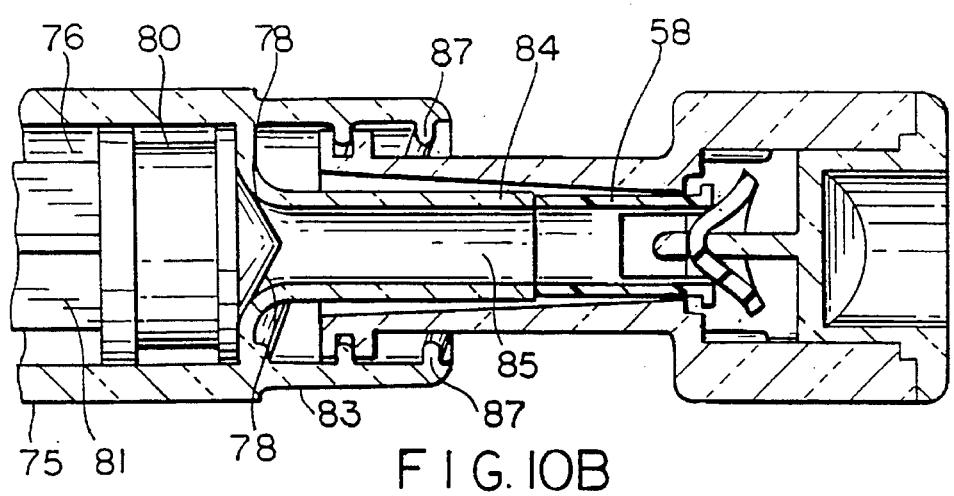
FIG. 10B is a cross-sectional view of the second infusion port of the dual-port medical infusion device of the first illustrative embodiment, taken along line 10B—10B of FIG. 2C, showing a needleless injection syringe connector connected to the second infusion port with its actuator portion engaged with and displacing the check valve plunger thereof so that the flexible check valve disc is arranged in its open configuration.
Figure 10C:
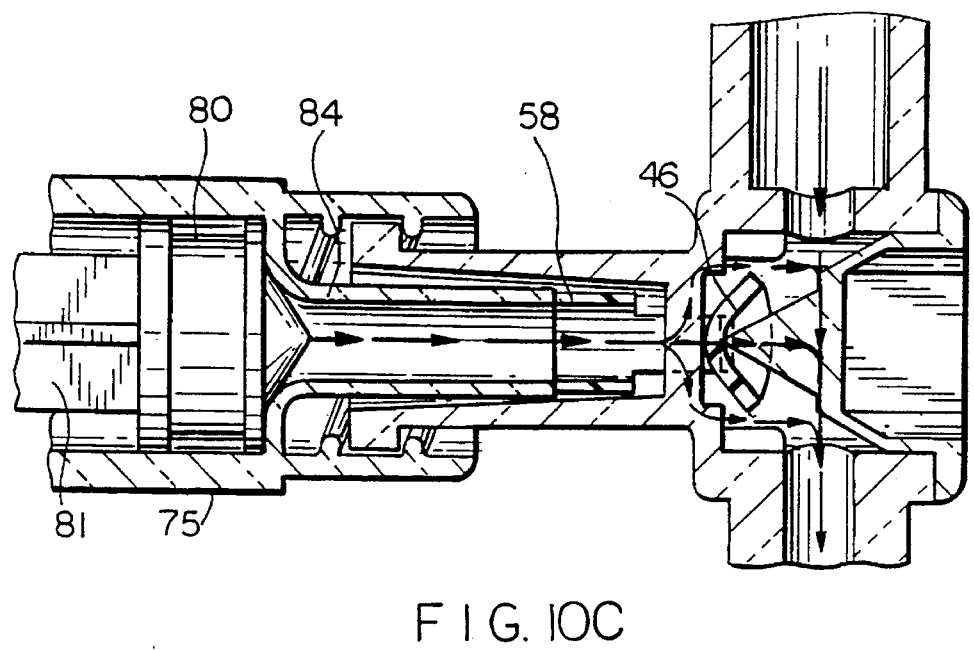
FIG. 10C is a cross-sectional view of the dual-port medical infusion device of the first illustrative embodiment, taken along line 10C—10C of FIG. 2C, showing an injection syringe connector connected to the second infusion port with its actuator portion engaged with and displacing the check valve plunger thereof so that the flexible check valve disc is arranged in its open configuration, so medication can be injected into the second infusion port.
Figure 10D:
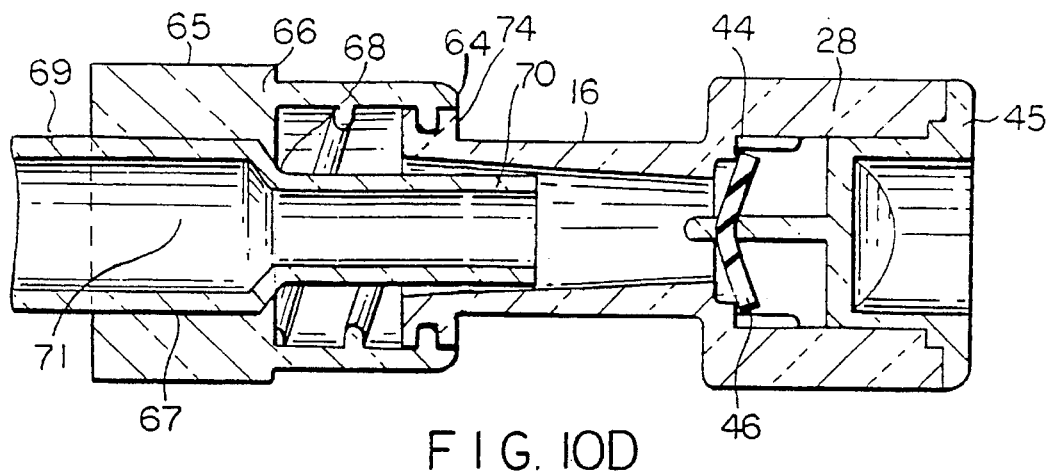
FIG. 10D is a cross-sectional view of the dual-port medical infusion device of an alternative embodiment of the present invention illustrated in FIG. 2C, in which the flexible check valve disc is actuated by a fluid pressure differential created across its check valve opening by a supply of medical fluid entering the infusion port associated therewith.
Figure 10E:
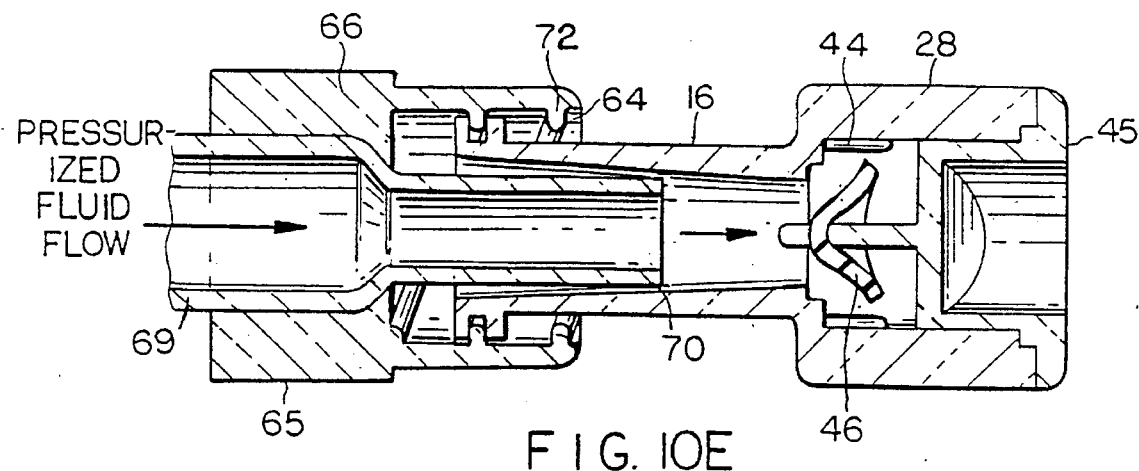
FIG. 10E is a cross-sectional view of the dual-port medical infusion device of FIG. 10D, showing a medical infusion tube connector connected to the first infusion port thereof, its flexible check valve disc rearranged into its open configuration by a fluid pressure differential created by a supply of medicational fluid entering the first infusion port of the medical infusion device, and the infused stream of medicational fluid infusing into the primary intravenous.
Figure 10F:
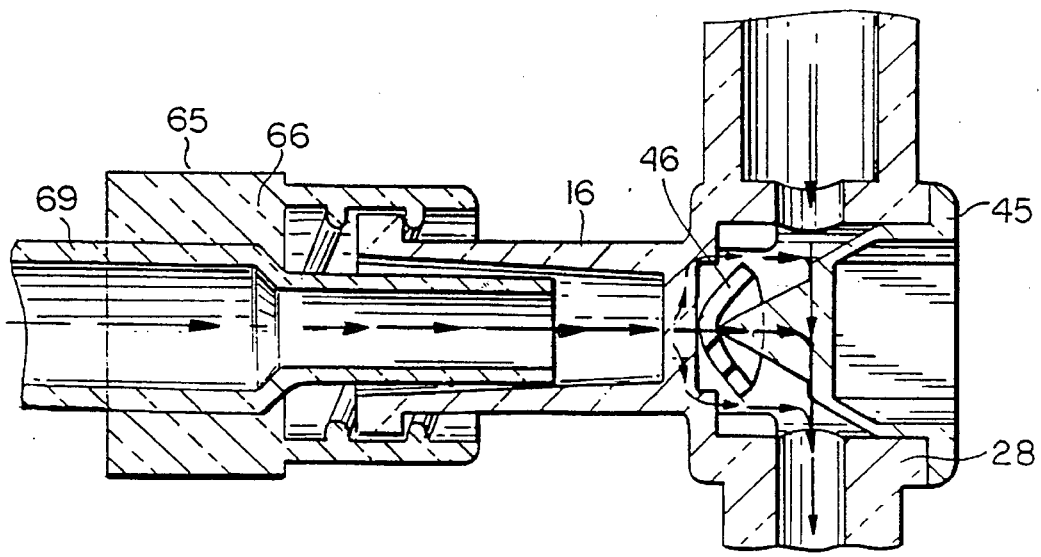
FIG. 10F is another cross-sectional view of the dual-port medical infusion device of FIG. 10D taken orthoganally to the cross-sectional view of FIG. 10E, showing the medical infusion tube connector connected to the first infusion port thereof, its flexible check valve disc rearranged into its open configuration by a fluid pressure differential created by a supply of fluid entering the first infusion port of the medical infusion device, and the infused stream of medicational fluid infusing into the primary intravenous stream passing through the check valve chamber of the device.

As shown in FIG. 10B, by completely rotating the syringe connector body portion 83 about the end of the infusion tube, the actuator portion 84 is displaced along the infusion tube until it engages and physically displaces the check valve plunger 58. In turn, the projections extending from the end of the check valve plunger reconfigure the flexible check valve disc 46 into its open configuration, as shown in FIG. 10B. In this configuration, the flexible check valve disc is pushed away from second annular surface 44, thus permitting infused fluid to flow from the interior volume within the infusion tube, into the interior volume of its associated check valve chamber, as illustrated in FIG. 10C. In this valve open configuration, fluid contained in fluid storage chamber 76 fills the interior volume of the infusion tube portion as rubber tip seal 80 is pushed inwardly and thereafter the syringe contents is permitted to flow through the check valve opening 34 formed at the check valve plane, shown in FIG. 4. As the fluid flows through the check valve opening, it enters the associated check valve chamber and directly mixes with the primary intravenous fluid stream flowing along the primary flow channel 13 of the multi-port infusion device.

Alternatively, the needless-injection syringe 22 described above may be used to withdraw a sample of primary fluid flowing through the check valve chamber of any of the medical infusion device of the present invention that permit two way flow. When used for this purpose, the fluid storage chamber of the syringe is empty, and the syringe plunger and rubber tip seal are pushed against fluid ejection opening 78 prior to connecting the syringe connector to the infusion port of the medical infusion device. Then, with syringe actuator engaging the check valve plunger and the flexible check valve disc reconfigured into its open configuration, the user slowly withdraws the plunger partially out of the fluid storage chamber of the syringe. The withdrawing action of the syringe plunger creates a partial vacuum at the infusion port, and causes primary fluid to flow out of the check valve chamber, through the opened check valve opening and out the infusion port into the fluid storage chamber of the syringe. When a sample of primary fluid has been acquired, the syringe can be disconnected from the infusion port by unscrewing the connector body portion. With nothing holding the plunger against the check valve disc, the original prebiasing of the disc will cause the disc to return to its closed position against annular surface A protective infusion port cap can be attached if desired or required to the infusion port.

Referring to FIGS. 10D–10F, an alternative embodiment of the multi-port medical infusion device is shown. Unlike the plunger-actuated medical infusion device of the first illustrative embodiment, the medical infusion device of FIGS. 10D–10F is fluid pressure actuated and thus does not require a check valve plunger 58. As shown in these figures, the medical infusion device of this embodiment is otherwise structurally identical to the medical infusion device of the first illustrative embodiment. Its function is somewhat different, however. As shown in FIG. 10D, when medical tubing connector 65 is connected to infusion port 14 or 15, actuator portion 70 is merely inserted into the infusion flow passageway of the infusion port and does not engage or displace anything. As shown in FIGS. 10E and 10F, a pressurized medical fluid is injected into the infusion port and flows towards the resilient check valve disc. Owing to the fact that the fluid pressure is greater within the interior volume of the infusion tube portion than within the interior volume of check valve chamber, a sufficient pressure differential is created across the check valve opening, causing the check valve disc to deform into its open configuration. Consequently, the medical fluid freely flows across the check valve opening, and directly infuses with the primary intravenous fluid stream passing through the interior volume of the check valve chamber as long as there is sufficient pressure differential. Notably, however, only one-way fluid infusion is possible using the medical infusion device of this alternative embodiment, whereas bi-directional fluid flow is possible with the first and other illustrative embodiments of the present invention. When the pressurized fluid flow is finished, there will no longer be a pressure differential to open the check valve disc. The prebiased disc will return to its closed position forming an annular seal with surface 44.

Having described the structure and function of the medical infusion device of the first illustrative embodiment of the present invention, a number of alternative embodiments ready come to mind. Such alternative embodiments of the present invention will be described below.

Referring to FIGS. 11–15, a second embodiment of the medical infusion device of the present invention is shown. Unlike the medical infusion device of the first illustrative embodiment, medical infusion device 90 has only a single infusion port 91 arranged axially with the primary fluid outlet port 92 of this device. As shown, the primary fluid inlet port 93 of this medical infusion device is disposed at an acute angle (less than 90 degrees) with respect to the axis, along which infusion port 91 and primary fluid outlet port 92 are arranged.

Figure 11:
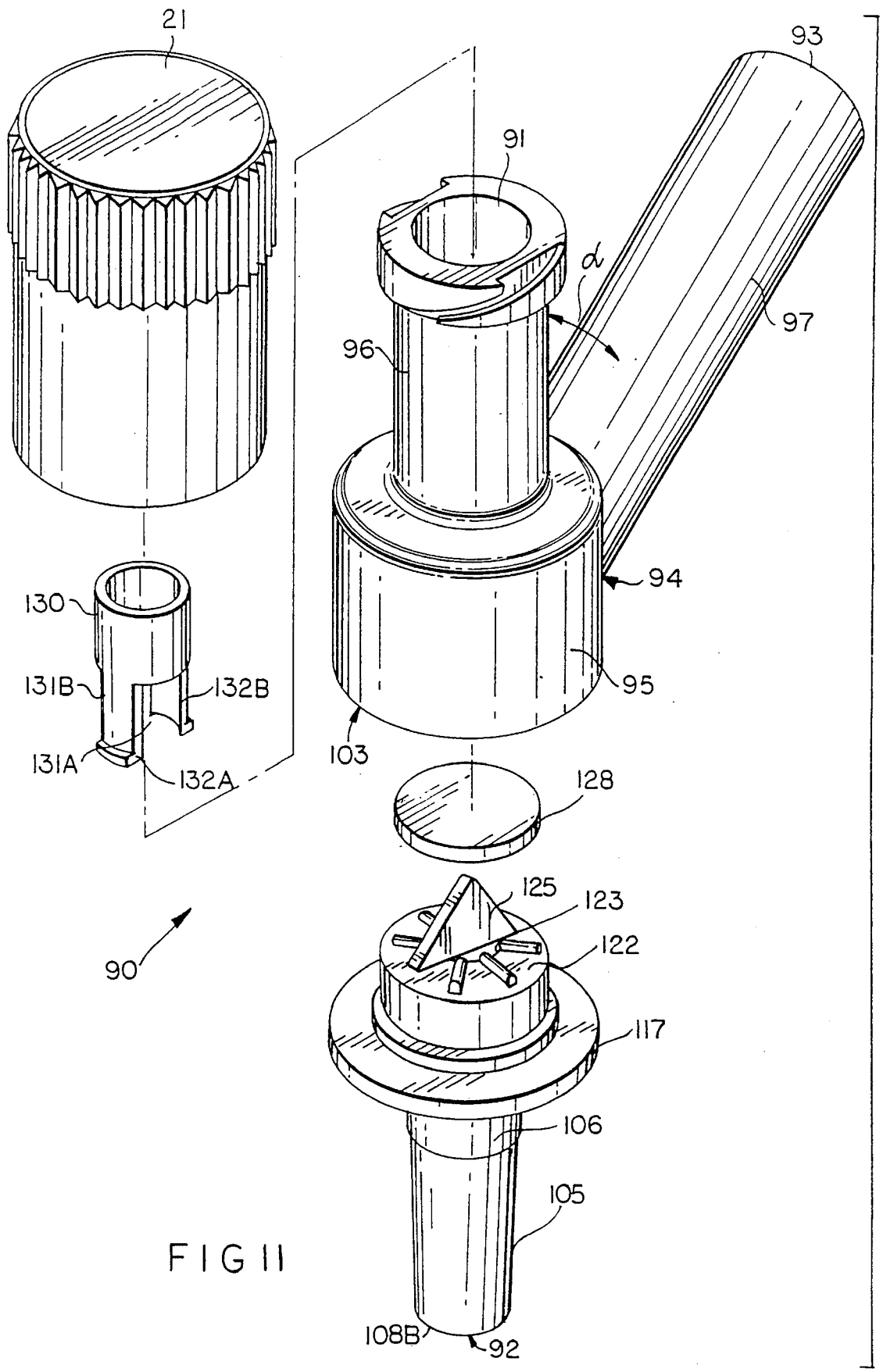
FIG. 11 is an exploded, partially fragmented perspective view of the single-port, Y-type, medical infusion device of the second illustrative embodiment of the present invention, showing the protective infusion port cap, the infusion tube portion and the check valve chamber, the flexible check valve disc, the check valve plunger, and the check valve support structure.

As shown in FIG. 11, medical infusion device 90 comprises a housing portion 94 comprising a check valve chamber 95, an infusion tube 96 extending from the check valve chamber, and a primary inlet tube 97 extending from check valve chamber.

Figure 15:
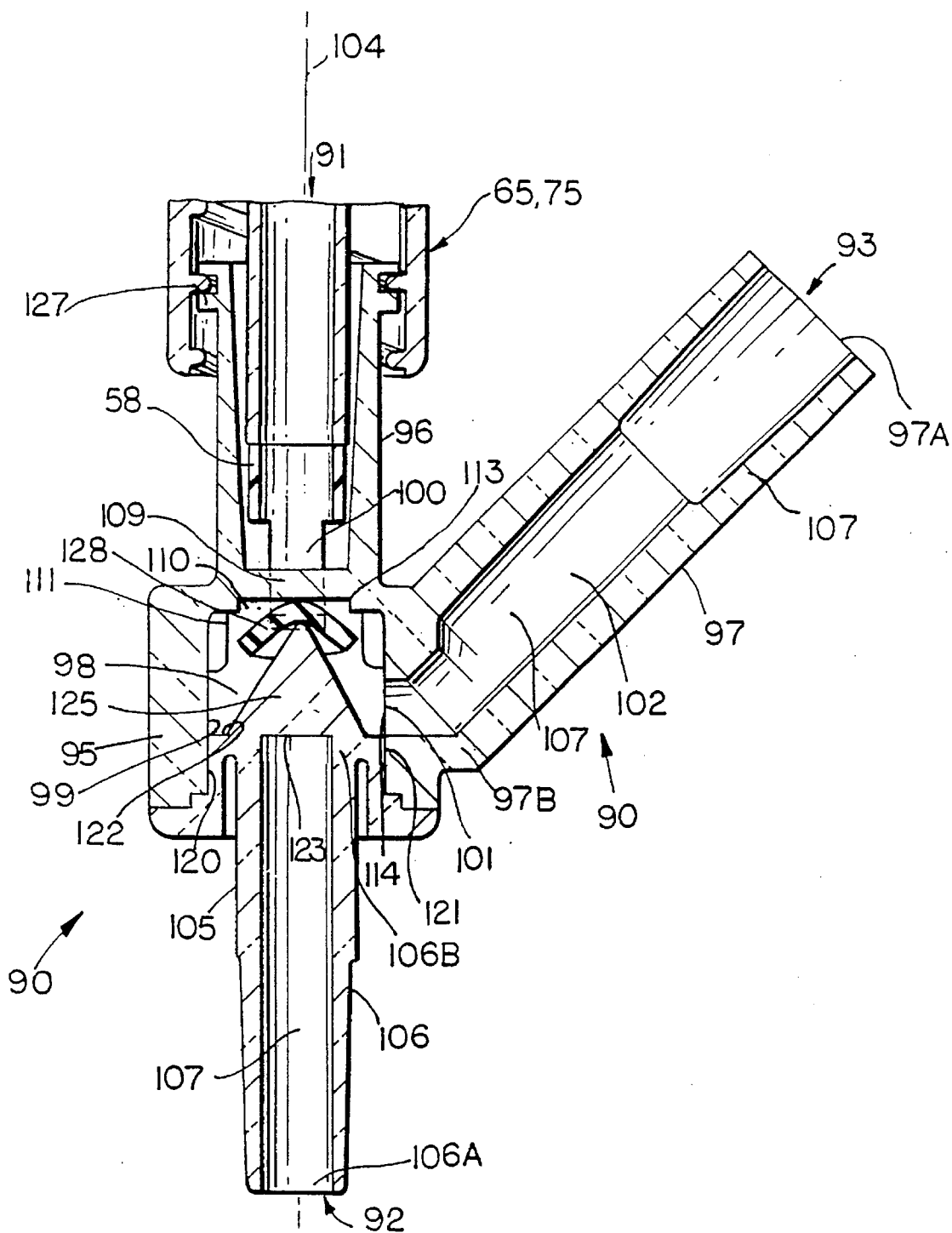
FIG. 15 is a cross-sectional view of the single-port medical infusion device of FIG. 11, showing a needleless injection syringe connector connected to the infusion port thereof with its actuator portion engaging and displacing the check valve plunger so that the flexible check valve disc is arranged in its open configuration.

As best shown in FIG. 15, check valve chamber 95 of medical infusion device 90 comprises a number of structural features, namely: an interior volume 98 surrounded by a wall surface 99 defined by a truncated cylindrical geometry and having optional planar side surface portions 120 and 121; a check valve opening 100 formed in the upper portion of the check valve chamber; a side wall opening 101 formed in the side wall surface of the check valve chamber and extending into the interior volume 102 of primary inlet tube portion 97; and a chamber opening 103 axially aligned with the check valve opening 100 along a longitudinal axis 104. As shown, the infusion port of medical infusion device 90 comprises cylindrical tube portion 96 which is integrally connected to check valve chamber 95. As shown, infusion tube portion 96 has an interior volume surrounded by interior wall surfaces defined by cylindrical geometry. Notably, check valve opening 100 is disposed at the interface between the interior volume of the check valve chamber and the interior volume of infusion tube portion 96.

As shown in FIGS. 11 and 15, the primary fluid inlet tube portion 97 has first and second end portions 97A and 97B, respectively. The first end portion 97A functions as the primary fluid inlet port, whereas the second end portion 97B is connected to side wall opening 101 formed in the check valve chamber. As shown in FIG. 15, check valve support structure 105 of the second illustrative embodiment has a primary fluid outlet tube portion 106 integrally attached thereto. The primary fluid outlet tube portion also has first and second end portions 106A and 106B. The first end portion 106A functions as the primary fluid outlet port of the medical infusion device, whereas the second end portion 106B opens into the interior volume 98 of the check valve chamber 95 of the medical infusion device 90. As shown in FIG. 15, a primary fluid passageway 107 continuously extends from a primary fluid inlet opening 108A in primary fluid inlet port 97A to primary fluid outlet portion 106A and out primary fluid outlet opening 108B, after passing through primary inlet tube portion 97, check valve chamber 95, and primary outlet tube portion 106.

As shown in FIG. 15, check valve opening 100 has a substantially circular geometry and may be bisected by an optional check valve bar 109 that is disposed within the plane of the check valve opening. As illustrated in, check valve opening 100 has a pair of annular recesses 110 and 111 which are disposed adjacent the upper portion of the check valve chamber 95. As shown, first annular recess 110 is spaced apart from second annular recess 111. Associated with first and second annular recesses 110 and 111 are first and second annular support surfaces 113 and 114, respectively. The first annular surface 113 is adjacent the end of cylindrical interior volume of the infusion tube, whereas the second annular surface 114 is disposed adjacent the upper portion of the interior volume of the check valve chamber.

Figure 12:
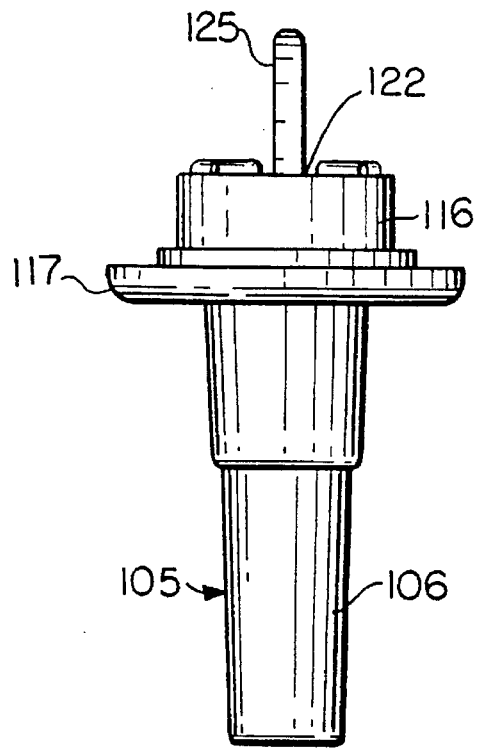
FIG. 12 is a first elevated side view of the valve support member removed from the medical infusion device of the second illustrative embodiment, and showing the end of the check valve support projection of the second illustrative embodiment.
Figure 13:
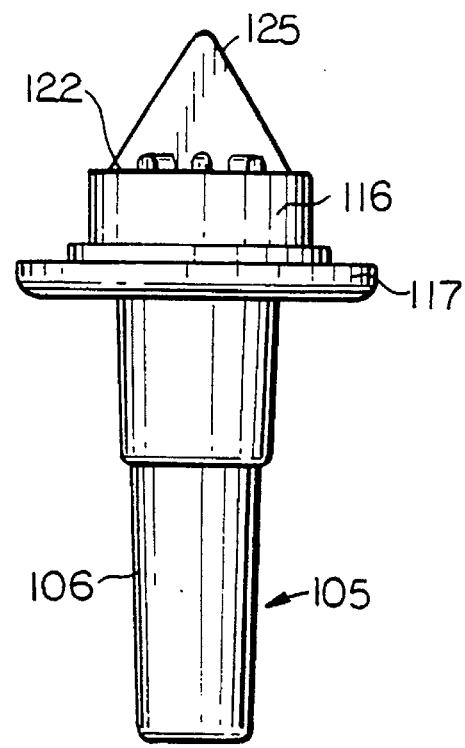
FIG. 13 is a second elevated side view of the check valve support structure removed from the medical infusion device of the second illustrative embodiment, and showing the side of the check valve support projection thereof.
Figure 14:
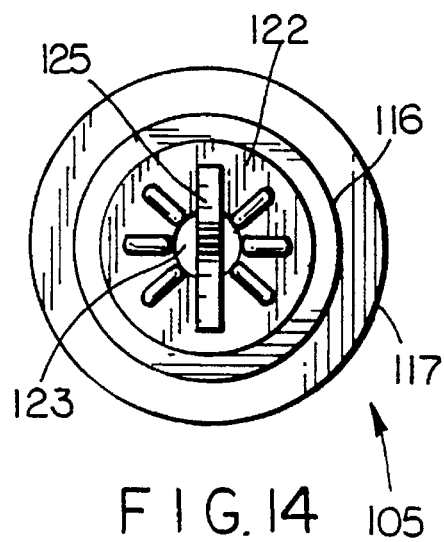
FIG. 14 is a plan view of the check valve support structure shown removed from the check valve chamber of the medical infusion device of the second embodiment of the present invention.
Figure 14A:
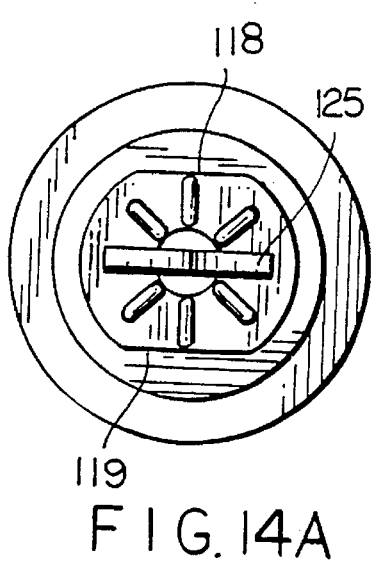
FIG. 14A is a plan view of the check valve support structure with optional planar side surfaces.

As best shown in FIGS. 12–14, check valve support structure 105 of the second illustrative embodiment has a number of structural features, namely: a truncated cylindrical base portion 116 having a hollow interior; an annular-shaped cover flange 117 extending radially outward from the bottom portion of truncated cylindrical base portion; a planar top fluid-flow surface 122, extending within a plane disposed substantial parallel to annulus-shaped cover flange 117; a fluid flow aperture 123 formed through planar top fluid-flow surface 122; and a primary fluid outlet tube portion 106 which extends from the central fluid-flow aperture 123, along the longitudinal axis 104. The outer dimensions of the truncated cylindrical base portion 116 are slightly less than the interior dimensions of the truncated cylindrical interior volume 98 of the check valve chamber. As shown in FIG. 14A, check valve support structure 105A has an optional pair of planar side surfaces 118 and 119 for engagement with planar side wall surfaces 120 and 121, respectively.

As shown in FIGS. 12–14, check valve support structure 105 also includes check valve support element 125 which, as in the first illustrative embodiment, is of a triangular-shaped geometry. As discussed previously, support element 125 can be a variety of shapes. As shown, check valve support element 125 has a very thin width dimension. When check valve support structure 105 is installed within its associated check valve chamber, fluid flow obstruction is minimized along its longitudinal dimension.

As shown in FIG. 15, the longitudinal extent of the check valve support element 125 may be aligned with optional planar side fluid flow surfaces 118 and 119, and extends substantially perpendicularly from planar top fluid flow surface 122. When the check valve support structure is installed within check valve chamber 95, planar side surfaces formed on truncated cylindrical base portion 116 register with and engage the wall surfaces of the truncated cylindrical interior volume 98. When the check valve structure is installed within check valve chamber 95 as shown in these figures, the check valve chamber opening 193 is closed off by the truncated cylindrical base portion 116, which functions a chamber opening cover.

As shown in FIGS. 11 and 15, infusion tube portion 96 bears exteriorly disposed threads 127 formed on the outer end portion thereof. The function of these exterior threads is to permit one to easily connect to the infusion port, either the connector portion of an infusion tube connector 65, or the connector portion 75 of a needleless injection syringe 22, as illustrated in the first illustrative embodiment.

As shown in FIGS. 11 and 15, flexible check valve disc 128 is installed through check valve chamber opening 103 during manufacture and is seated against check valve annular surface 114. Then, check valve support structure 105 is inserted through check valve chamber opening 103 and check valve support element 125 engages the bottom portion of the flexible check valve disc, prebiasing the disc against annular surface 114 forming an annular seal. The disc is thus in a normally closed position.

Medical infusion device 90 can permit one way flow through infusion port 91 (no plunger) or two way flow when a plunger is used. For illustrative purposes, a two way flow device will be described in further detail. A check valve plunger 130 is inserted through the end opening formed at the infusion port, and pushed towards the check valve opening for installation within the interior volume of the cylindrical infusion tube 96. An illustrative embodiment of the check valve plunger 130 is realized as a cylindrical tube having a pair of diametrically opposing side wall cut-out portions 131A and 131B. These side wall cut-out portions 131A and 131B are laterally separated by two diametrically opposed wall portions 132A and 132B which extend along the longitudinal extent of the check valve plunger. As shown in FIGS. 11 and 15, wall portions 132A and 132B terminate in transverse projections 133A and 133B, respectively, and extend radially outward from each other in a direction substantially perpendicular to the longitudinal axis 104. When slid along the interior of the cylindrical infusion tube portion 96, wall portions 132A and 132B retract inwardly until projections 133A and 133B reach and snap into first annular recess 110, above flexible check valve disc 128. When the check valve components are completely assembled in the manner illustrated in FIGS. 11 and 15, the upper surface of flexible check valve disc 128 engages second annular surface 114, to effect a valve seal, while the central portion of the flexible check valve disc is supported by check valve support element 125. In this assembled state, the resilient check valve disc is deemed to be in its normally closed configuration. However, for illustration purposes, flexible check valve disc 128 is shown configured in its open configuration in FIG. 15. Also as shown, optional check valve bar 109 can be used to prevent blow out of the disc through inlet port 91.

Figure 16:
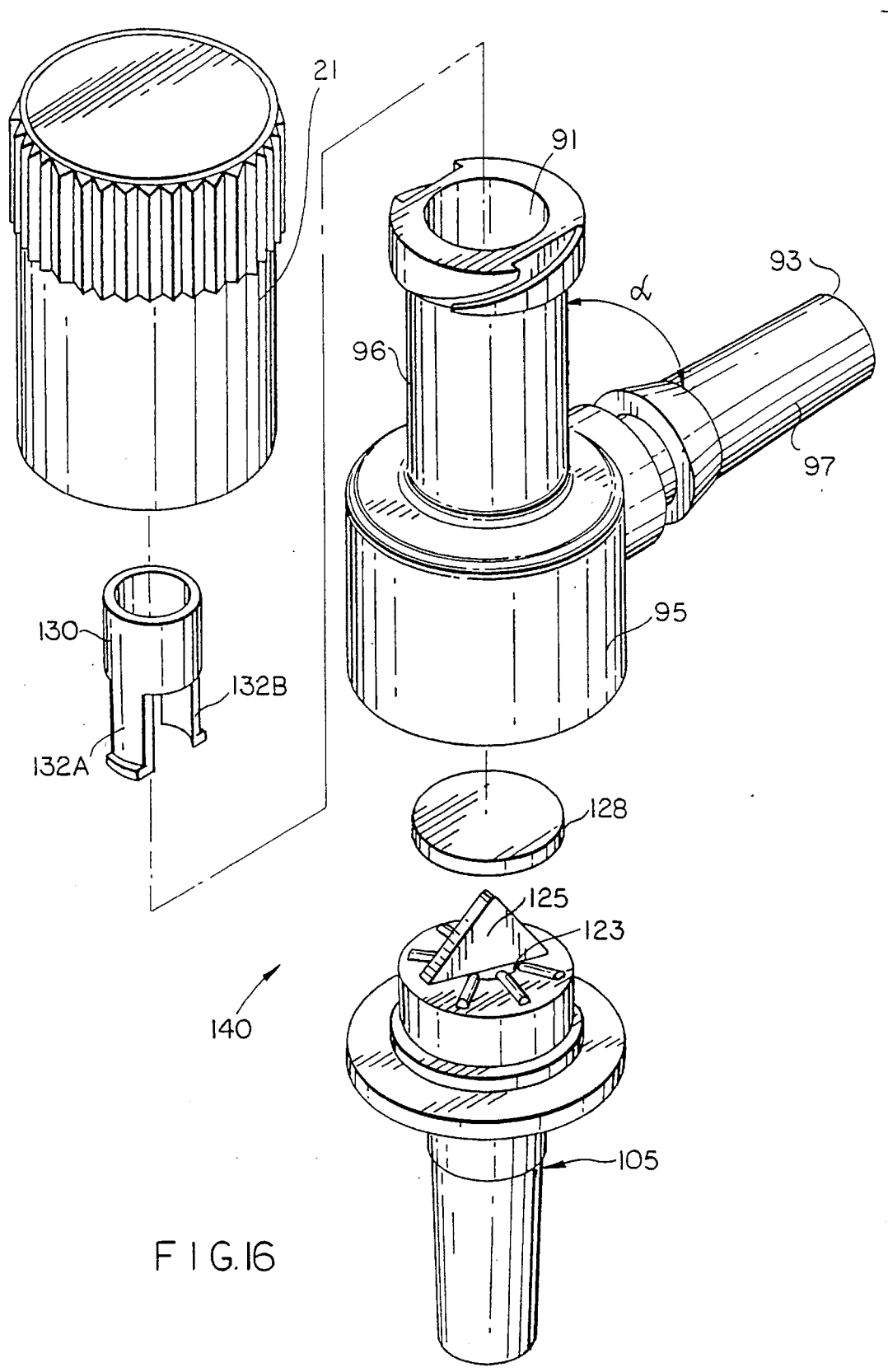
FIG. 16 is an exploded, perspective partially fragmented view of the single-port, T-type, medical infusion device of the third illustrative embodiment of the present invention, showing the protective infusion port cap, the infusion port and check valve chamber, the flexible check valve disc, the check valve plunger, and the check valve support structure.
Figure 17:
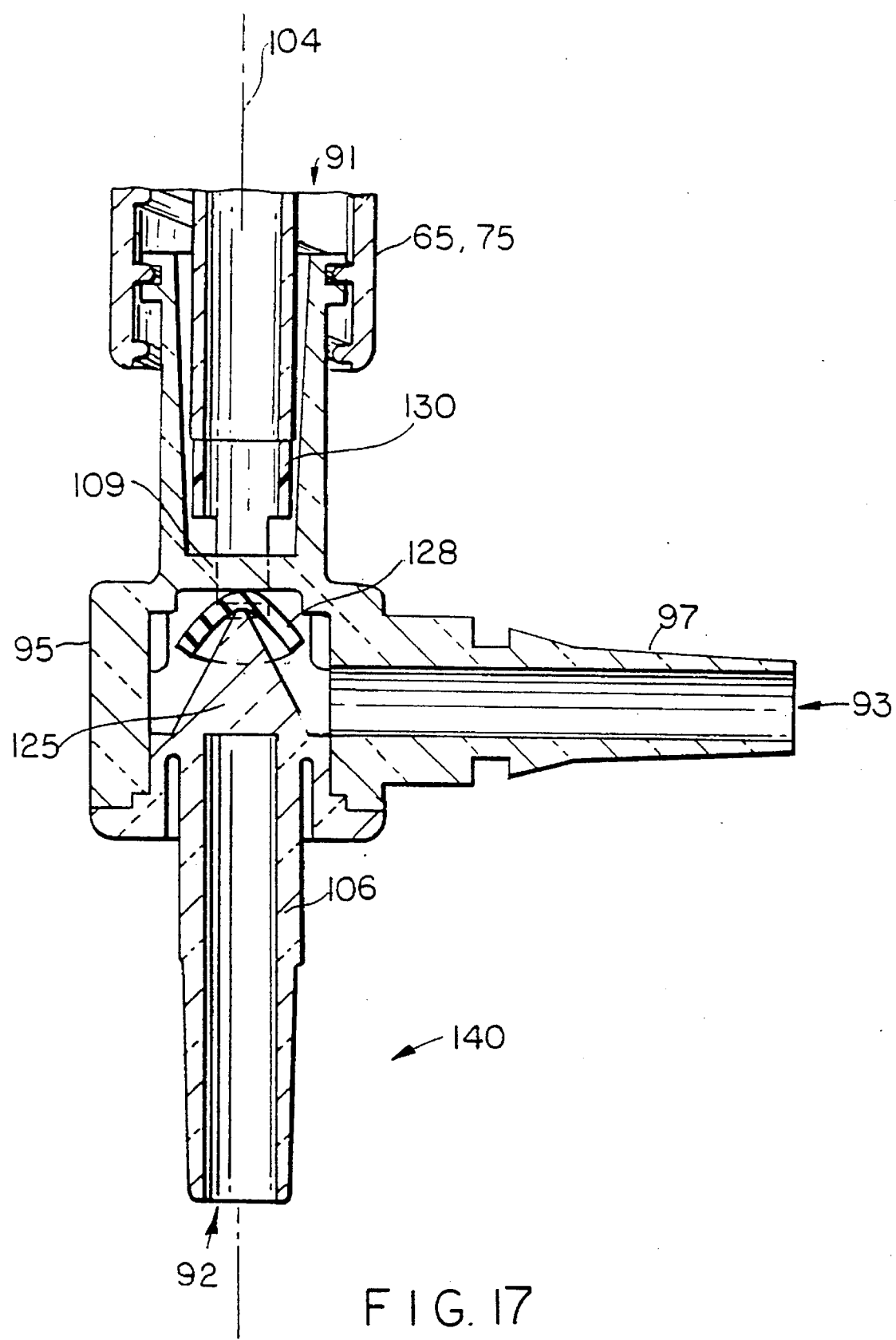
FIG. 17 is a cross-sectional view of the single-port medical infusion device of FIG. 16, showing a needleless injection syringe connector connected to the infusion port with its actuator portion engaging and displacing the check valve plunger so that the flexible check valve disc is arranged in its open configuration.

Referring to FIGS. 16–17, a third embodiment of the medical infusion device of the present invention is shown. The primary difference between the medical infusion devices of FIGS. 11–15 and FIGS. 16–17 is that the angle formed between the longitudinal axis of the primary fluid inlet port 93 of medical infusion device 140 and its infusion tube 96 is about 90 degrees, whereas this angle is about 45 degrees in medical infusion device 90 of the second illustrative embodiment. In all other respects, the structural and functional features of these embodiments of the present invention are the same.

The primary difference between medical infusion devices 145 (FIGS. 18–19B) and 90 (FIGS. 11–15) relates to the design and construction of check valve plungers and check valve apertures. As discussed previously, multiple designs and plunger configurations can be used in the medical infusion devices of the present invention. FIG. 18 shows a check valve plunger 146 as a tubular structure having a pair of diametrically spaced apart fluid-flow apertures 147A and 147B formed in the lower portion thereof. The fluid flow apertures permit flow through the device and across the disc. Any type of spacing or holes would accomplish this stated purpose. This illustrative embodiment is shown without the optional check valve bar 40 or 109.

In the medical infusion device of FIG. 18, the outer diameter of check valve plunger 146 is slightly smaller than the inner diameter of cylindrical infusion tube portion 96 of the medical infusion device. As shown in FIG. 19A, infusion tube portion 96 has an enlarged annular recessed section 148 formed towards the check valve opening. The length of enlarged annular recess 148 is equal or greater than the length of plunger 146. The recessed portion 148 provides a housing for the plunger so that it is entrapped within fusion tube 96. Unlike the earlier plungers shown, there are no transverse projections 62A, 62B, 133A and 133B to hold the plunger in place. In all other respects, the structural and functional features of the fourth illustrative embodiment of the present invention are the substantially the same as those provided in the third illustrative embodiment.

During manufacture of medical infusion device 145, plunger 146 may be inserted through the check valve chamber opening 103, and into and along recessed section 148 until it contacts (i.e., engages) upper annular surface 148A formed at the end of annular recessed section 148, as shown in FIG. 19A. Flexible check valve disc 128 is then inserted through the check valve chamber opening 103 and against the annular surface 149 formed in the upper portion of the check valve chamber. Thereafter, check valve support structure 105 is installed through the check valve chamber opening 103 so that it rests in proper registration within the interior volume of the check valve chamber. Upon completion of this manufacturing step, the tip portion of the check valve support element 125 will engage the bottom of check valve disc 128 and deform it slightly against surface 149 to form an annular seal. Thereafter, the check valve support structure 105 is then sonically welded or solvently bonded to the interior side wall surfaces of check valve chamber 95 as hereinbefore described. When completely assembled, the flexible check valve disc is disposed in its normally closed configuration, as shown in FIG. 19A.

Any of the medical fluid sources described above can be connected to the infusion port of medical infusion device 145 by way of suitable actuatable-connectors (e.g., infusing tubing connector 65 or syringe connector 83). When the connector of an infusion source is arranged in its actuation position, the check valve plunger 146 is displaced within annular recess section 148 in the infusion tube portion of the device, and the flexible valve disc reconfigured into an open configuration, permitting fluid to flow along the infusion tube, through fluid-flow apertures 147A and 147B, and into primary fluid flow channel 107 passing through the infusion device, as shown in FIG. 19B.

Figure 20:
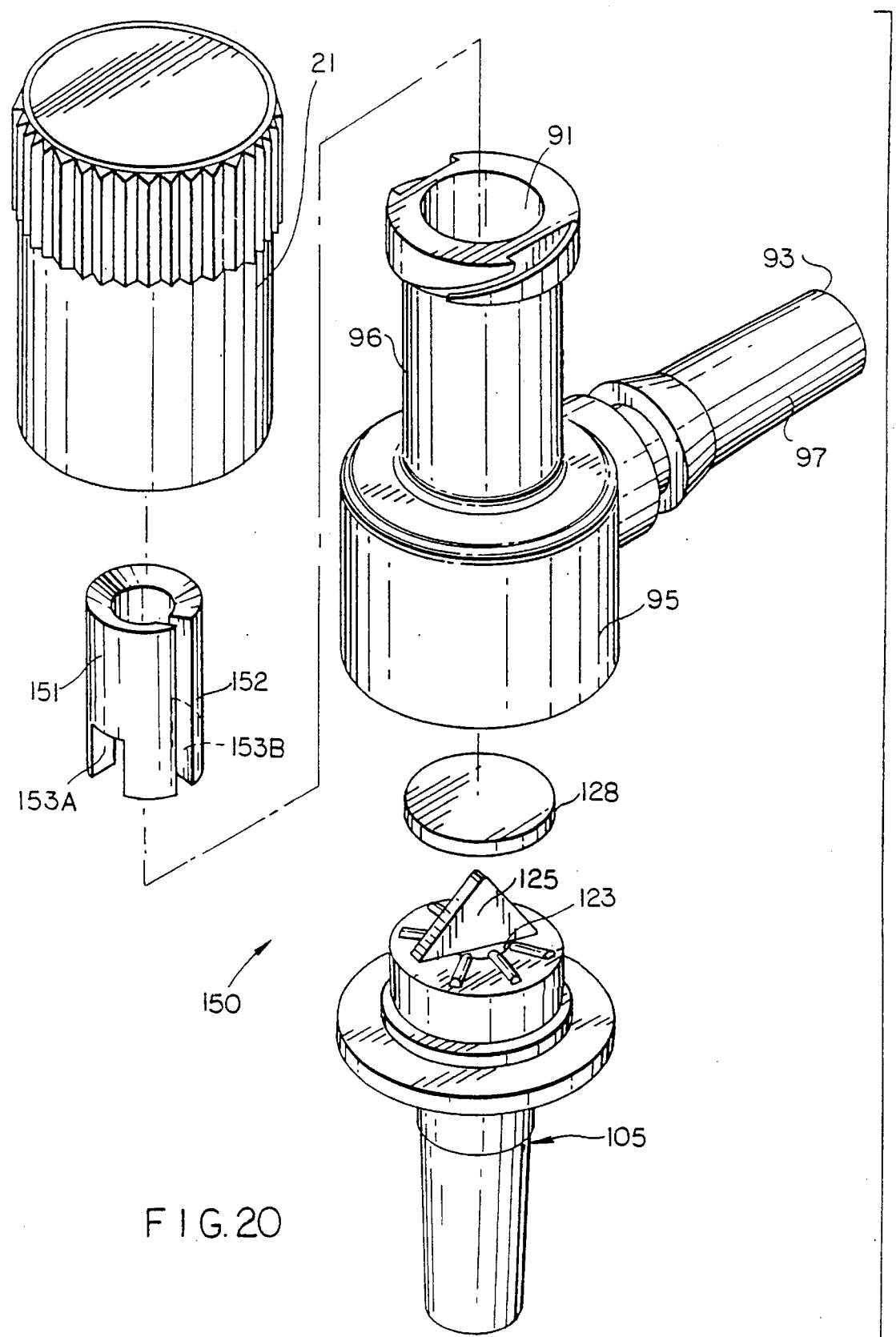
FIG. 20 is an exploded, perspective partially fragmented view of the single-port, T-type, medical infusion device of the third illustrative embodiment of the present invention, showing the protective infusion port cap, the infusion port and check valve chamber, the flexible check valve disc, the check valve plunger, and the check valve support structure thereof.

In FIGS. 20–21B an additional embodiment of the present invention is shown as medical infusion device 150. This device is similar to the medical infusion device 140 except that the check valve plunger 151 of medical infusion device 150 has a longitudinal slit 152 and a pair of fluid-flow slits 153A and 153B formed in the tubular wall portion thereof, as shown. The length of tubular structure 151 is less than or equal to the length of enlarged annular recess 148 formed in the infusion tube portion 96. In all other respects, the structural and functional features of the fifth illustrative of the present invention are the substantially the same as those provided in the fourth illustrative embodiment.

As shown in FIG. 20, during manufacture, slit 152 permits the check valve plunger 151 to be compressed in its diameter dimension sufficiently enough to be inserted through the end opening 91 at the infusion port side of the medical infusion device 150. When check valve plunger 152 is slid beyond the narrower section of infusion tube portion 96, and approaches enlarged recess section 148, the check valve plunger 151 is permitted to expand to its normal relaxed diameter and thus fit into its recess section 148, as shown in FIGS. 21A and 21B. Depending on the manufacturing, the plunger 151 can alternatively be inserted through the check valve chamber opening 103. Actuation of check valve plunger 151 as described in the other illustrative embodiments permits the flexible check valve disc 128 to be configured into its open configuration, as shown in FIG. 21B. Slit 152 provides the additional advantage that different shaped and lengthened actuator portions 70 and 84 will no longer just push against the plunger but can mate with the plunger. The slit 152 allows the plunger to expand permitting this fit to occur.

Preferably, the main housing of each medical infusion device of the present invention is integrally formed using conventional injection molding plastics. Preferably, each check valve support structure 45 and 105 is also manufactured using injection molding techniques. While polycarbonate plastic is the material of choice from which the medical infusion devices are to be made, other materials may be used with excellent results. In any case, it is preferred to use materials having optically transparent properties as this will enable the user of the medical infusion device to visually monitor the flow of infused fluids into the primary intravenous stream during operation of the device. Preferably, each check valve support structure of the illustrative embodiments is either sonically welded or solvently bond in place within its associated check valve chamber. This operation can be carried out using either robotic or manual manufacturing techniques known in the art, without compromising the performance or operation of the medical infusion device so constructed.

While the particular illustrative embodiments of the medical infusion device shown and described above will be useful in many medical and health-care related applications, further modifications to the present invention will occur to persons with ordinary skill in the art. All such modifications are deemed to be within the scope and spirit of the present invention defined by the appended claims to invention.

What is claimed is:

1. A medical infusion device for infusing a medical fluid into a primary fluid stream, comprising:

(1) a check valve chamber having an interior volume, surrounded by a chamber wall surface of three dimensional extent, a check valve opening formed through said chamber wall surface, and first and second primary fluid flow openings;

(2) a flexible check valve element disposed immediately adjacent said check valve opening and having a normally closed configuration and an open configuration;

(3) a check valve support structure for supporting said flexible check valve element against said check valve opening in said normally closed configuration so as to prevent the flow of fluid through said check valve opening in said normally closed configuration, and permitting said check valve element to reconfigure into an open configuration so as permit the flow of fluid through said check valve opening in said open configuration;

(4) a primary fluid inlet port for connecting said medical infusion device to a first connector capable of providing a primary fluid stream, said primary fluid inlet port further including a primary fluid inlet opening and a primary fluid inlet flow passageway extending from said primary fluid inlet opening through said first primary fluid flow passageway and into the interior volume of said check valve chamber;

(5) a primary fluid outlet port for connecting said medical infusion device to a second connector capable of receiving said primary fluid stream, said primary fluid outlet port further including a primary fluid outlet opening and a primary fluid outlet flow passageway extending from said primary fluid outlet flow opening through said second primary fluid flow passageway and into the interior volume of said check valve chamber;

(6) a primary fluid flow passageway continuously extending from said primary fluid inlet port to said primary fluid outlet port by way of passage through said primary fluid inlet opening, said primary fluid inlet flow passageway, said first primary fluid flow opening, said interior volume of said check valve chamber, said second primary fluid flow opening, said primary fluid outlet flow passageway, and said primary fluid outlet opening;

(7) an infusion port for connecting said medical infusion device to a third connector operably connected to a medical fluid supply means for supplying fluid through said third connector for infusion into said primary fluid stream, said infusion port further including an infusion fluid inlet opening, and an infusion fluid inlet flow passageway extending from said infusion fluid inlet opening through said check valve opening into the interior volume of said check valve chamber; and wherein, when said flexible check valve element is in said open configuration, said third connector is connected to said infusion port, and said medical fluid supply means supplies medical fluid through said third connector into said infusion fluid inlet flow passageway, then said medical fluid is permitted to flow from said medical fluid supply means through said infusion fluid inlet opening, along said infusion fluid inlet flow passageway, through said check valve opening, and therefrom directly into said primary fluid stream passing along said primary fluid flow passageway.

2. The medical infusion device of claim 1, wherein said flexible check valve element is a flexible check valve disc, and wherein said check valve opening comprises a circular opening and an annular surface extending about said circular opening and facing the interior volume of said check valve chamber.

3. The medical infusion device of claim 2, wherein said flexible check valve disc has an upper surface that engages said annular surface when said flexible check valve disc is configured in said normally closed configuration.

4. The medical infusion device of claim 2, wherein said circular opening is disposed within a plane, and said check valve support structure extends substantially perpendicular to said plane and engages said central portion of said flexible check valve disc when said flexible check valve disc is configured in said normally closed configuration.

5. The medical infusion device of claim 4, wherein said check valve opening comprises a check valve bar disposed substantially across said circular opening so as to bisect the same, and wherein said flexible check valve disc is supported between said check valve support element, said annular surface and said check valve bar when said flexible check valve disc is configured in said normally closed configuration.

6. The medical infusion device of claim 5, wherein said first and second primary fluid flow openings are disposed along a primary fluid flow axis extending through the interior of said check valve chamber and the thin planar region within which said check valve support element is disposed.

7. The medical infusion device of claim 4, wherein said check valve support structure further comprises a base portion having a substantially planar top fluid-flow surface, from which said check valve support element extends.

8. The medical infusion device of claim 7, wherein said check valve support element comprises a triangular structure having a base, and two side surfaces extending from said base and converging towards a tip portion which engages the central portion of said flexible check valve disc.

9. The medical infusion device of claim 1, wherein said primary fluid inlet port and said primary fluid outlet port are disposed along a first reference axis extending along said primary fluid flow passageway, and wherein said infusion port and said check valve opening are disposed along a second reference which intersects with said first reference axis at an angle of about 90 degrees.

10. The medical infusion device of claim 1, wherein said primary fluid inlet port and said primary fluid outlet port are disposed along a first reference axis extending along said primary fluid flow passageway, and wherein said infusion port and said check valve opening are disposed along a second reference which intersects with said first reference axis at an acute angle less than about 90 degrees.

11. The medical infusion device of claim 1, wherein said a check valve chamber, said check valve support structure, said primary fluid inlet port, said primary fluid outlet port, and said infusion port are made from an optically transparent plastic.

12. The medical infusion device of claim 11, wherein said optically transparent plastic is polycarbonate.

13. The medical infusion device of claim 2, wherein said flexible check valve disc is made from silicone rubber.

14. The medical infusion device of claim 1, in combination with (1) a catheter for introducing said primary intravenous stream into the body of a patient, (2) a first section of flexible medical tubing having a first end connectable to said catheter and a second end connectable to said primary fluid outlet port, and (3) a second section of flexible medical tubing having a first end connectable to said medical fluid supply means and a second end connectable to said primary fluid inlet port.

15. A medical infusion device for infusing a medical fluid into a primary fluid stream, comprising:

(1) a check valve chamber having an interior volume, surrounded by a chamber wall surface of three dimensional extent, a check valve opening formed through said chamber wall surface, a check valve chamber opening formed through said chamber wall surface and axially aligned with said check valve opening, and first and second primary fluid flow openings formed through said chamber wall surface;

(2) a flexible check valve element;

(3) a check valve support structure for supporting said flexible check valve element against said check valve opening in a normally closed configuration preventing the flow of fluid through said check valve opening in said normally closed configuration, said check valve support structure further including a base portion for closing off said check valve chamber opening in a sealed manner;

(4) a primary fluid inlet port for connecting said medical infusion device to a first connector capable of providing a primary fluid stream, said primary fluid inlet port further including a primary fluid inlet opening and a primary fluid inlet flow passageway extending from said primary fluid inlet opening through said first primary fluid flow passageway and into the interior volume of said check valve chamber;

(5) a primary fluid outlet port for connecting said medical infusion device to a second connector capable of receiving said primary fluid stream, said primary fluid outlet port further including a primary fluid outlet opening and a primary fluid outlet flow passageway extending from said primary fluid outlet flow opening through said second primary fluid flow passageway and into the interior volume of said check valve chamber;

(6) a primary fluid flow passageway continuously extending from said primary fluid inlet port to said primary fluid outlet port by way of passage through said primary fluid inlet opening, said primary fluid inlet flow passageway, said first primary fluid flow opening, said interior volume of said check valve chamber, said second primary fluid flow opening, said primary fluid outlet flow passageway, and said primary fluid outlet opening;

(7) an infusion port for connecting said medical infusion device to a third connector operably connected to a medical fluid supply means for supplying medical fluid through said third connector for infusion into said primary fluid stream, said infusion port further including an infusion fluid inlet opening, and an infusion fluid inlet flow passageway extending from said infusion fluid inlet opening through said check valve opening into the interior volume of said check valve chamber; and wherein, when said third connector is connected to said infusion port and said medical fluid supply means supplies medical fluid through said third connector into said infusion fluid inlet flow passageway, said medical fluid creates a pressure differential across said check valve opening causing said flexible check valve element to reconfigure from said normally closed configuration into an open configuration permitting said medical fluid to flow from said medical fluid supply means through said infusion port, along said infusion fluid inlet flow passageway, through said check valve opening, and into said primary fluid stream passing along said primary fluid flow passageway.

16. The medical infusion device of claim 15, wherein said check valve element is a flexible check valve disc, and said check valve opening comprises a circular opening and an annular surface extending about said circular opening and facing the interior volume of said check valve chamber, and wherein said flexible check valve disc has an upper surface that engages said annular surface when said flexible check valve disc is configured in said normally closed configuration.

17. The medical infusion device of claim 16, wherein said circular opening is disposed within a plane, and said check valve support structure extends substantially perpendicular to said plane and engages said central portion of said flexible check valve disc when said flexible check valve disc is configured in said normally closed configuration.

18. The medical infusion device of claim 17, wherein said check valve opening comprises a check valve bar disposed substantially within said plane and extending across said circular opening so as to bisect the same, and wherein said flexible check valve disc is supported between said check valve support element, said annular surface and said check valve bar when said flexible check valve disc is configured in said normally closed configuration.

19. The medical infusion device of claim 18, wherein said check valve support element has a width dimension of substantially planar geometry and said check valve bar has a width dimension of substantially planar geometry, and wherein said check valve support element and said check valve bar are arranged so that the width dimension of said check valve support element is aligned with the width dimension of said check valve bar to form a thin planar region.

20. The medical infusion device of claim 19, wherein said first and second primary fluid flow openings are disposed along a primary fluid flow axis extending through the interior of said check valve chamber and the thin planar region within which said check valve support element is disposed.

21. The medical infusion device of claim 18, wherein said check valve support structure further comprises a base portion having a substantially planar top fluid-flow surface, from which said check valve support element extends.

22. The medical infusion device of claim 21, wherein said check valve support element comprises a triangular structure having a base, and two side surfaces extending from said base and converging towards a tip portion which engages the central portion of said flexible check valve disc.

23. The medical infusion device of claim 15, wherein said primary fluid inlet port and said primary fluid outlet port are disposed along a first reference axis extending along said primary fluid flow passageway, and wherein said infusion port and said check valve opening are disposed along a second reference which intersects with said first reference axis at an angle of about 90 degrees.

24. The medical infusion device of claim 15, wherein said primary fluid inlet port and said primary fluid outlet port are disposed along a first reference axis extending along said primary fluid flow passageway, and wherein said infusion port and said check valve opening are disposed along a second reference which intersects with said first reference axis at an acute angle less than about 90 degrees.

25. The medical infusion device of claim 15, wherein said check valve chamber, said check valve support structure, said primary fluid inlet port, said primary fluid outlet port, and said infusion port are made from an optically transparent plastic.

26. The medical infusion device of claim 25, wherein said optically transparent plastic is polycarbonate.

27. The medical infusion device of claim 16, wherein said flexible check valve disc is made from silicone rubber.

28. The medical infusion device of claim 27, wherein said medical fluid supply means is a needleless injection syringe containing a supply of said medical fluid and connectable to said infusion port by way of said third connector.

29. The medical infusion device of claim 15, in combination with (1) a catheter for introducing said primary intravenous stream into the body of a patient, (2) a first section of flexible medical tubing having a first end connectable to said catheter and a second end connectable to said primary fluid outlet port, and (3) a second section of flexible medical tubing having a first end connectable to said medical fluid supply means and a second end connectable to said primary fluid inlet port.

30. A medical infusion device for infusing a medical fluid into a primary fluid stream, comprising:

(1) a check valve chamber having an interior volume, surrounded by a chamber wall surface of three dimensional extent, a check valve opening formed through said chamber wall surface, a check valve chamber opening formed through said chamber wall surface and axially aligned with said check valve opening, and a first primary fluid flow opening formed through said chamber wall surface;

(2) a flexible check valve element;

(3) a check valve support structure for supporting said flexible check valve element against said check valve opening in a normally closed configuration preventing the flow of fluid through said check valve opening in said normally closed configuration, said check valve support structure further including a base portion for closing off said check valve chamber opening in a sealed manner, and a second primary fluid flow opening formed in said base portion;

(4) a primary fluid inlet port for connecting said medical infusion device to a first connector capable of providing a primary fluid stream, said primary fluid inlet port further including a primary fluid inlet opening and a primary fluid inlet flow passageway extending from said primary fluid inlet opening through said first primary fluid flow passageway and into the interior volume of said check valve chamber;

(5) a primary fluid outlet port for connecting said medical infusion device to a second connector capable of receiving said primary fluid stream, said primary fluid outlet port further including a primary fluid outlet opening and a primary fluid outlet flow passageway extending from said primary fluid outlet flow opening through said second primary fluid flow passageway and into the interior volume of said check valve chamber;

(6) a primary fluid flow passageway continuously extending from said primary fluid inlet port to said primary fluid outlet port by way of passage through said primary fluid inlet opening, said primary fluid inlet flow passageway, said first primary fluid flow opening, said interior volume of said check valve chamber, said second primary fluid flow opening, said primary fluid outlet flow passageway, and said primary fluid outlet opening;

(7) an infusion port for connecting said medical infusion device to a third connector operably connected to a medical fluid supply means for supplying medical fluid through said third connector for infusion into said primary fluid stream, said infusion port further including an infusion fluid inlet opening, and an infusion fluid inlet flow passageway extending from said infusion fluid inlet opening through said check valve opening into the interior volume of said check valve chamber; and wherein, when said third connector is connected to said infusion port and said medical fluid supply means supplies medical fluid through said third connector into said infusion fluid inlet flow passageway, said medical fluid creates a pressure differential across said check valve opening causing said flexible check valve element to reconfigure from said normally closed configuration into an open configuration permitting said medical fluid to flow from said medical fluid supply means through said infusion fluid inlet port, along said infusion fluid inlet flow passageway, through said check valve opening, and into said primary fluid stream passing along said primary fluid flow passageway.

31. The medical infusion device of claim 30, wherein said flexible check valve element is a flexible check valve disc, and said check valve opening comprises a circular opening and an annular surface extending about said circular opening and facing the interior volume of said check valve chamber, and wherein said flexible check valve disc has an upper surface that engages said annular surface when said flexible check valve disc is configured in said normally closed configuration.

32. The medical infusion device of claim 31, wherein said circular opening is disposed within a plane, and said check valve support structure extends substantially perpendicular to said plane and engages said central portion of said flexible check valve disc when said flexible check valve disc is configured in said normally closed configuration.

33. The medical infusion device of claim 32, wherein said check valve opening comprises a check valve bar disposed substantially within said plane and extending across said circular opening so as to bisect the same, and wherein said flexible check valve disc is supported between said check valve support element, said annular surface and said check valve bar when said flexible check valve disc is configured in said normally closed configuration.

34. The medical infusion device of claim 33, wherein said check valve support element has a width dimension of substantially planar geometry and said check valve bar has a width dimension of substantially planar geometry, and wherein said check valve support element and said check valve bar are arranged so that the width dimension of said check valve support element is aligned with the width dimension of said check valve bar to form a thin planar region.

35. The medical infusion device of claim 34, wherein said first and second primary fluid flow openings are disposed along a primary fluid flow axis extending through the interior of said check valve chamber and the thin planar region within which said check valve support element is disposed.

36. The medical infusion device of claim 33, wherein said check valve support structure further comprises a base portion having a substantially planar top fluid-flow surface, from which said check valve support element extends.

37. The medical infusion device of claim 36, wherein said check valve support element comprises a triangular structure having a base, and two side surfaces extending from said base and converging towards a tip portion which engages the central portion of said flexible check valve disc.

38. The medical infusion device of claim 30, wherein said primary fluid inlet port and said primary fluid outlet port are disposed along a first reference axis extending along said primary fluid flow passageway, and wherein said infusion port and said check valve opening are disposed along a second reference which intersects with said first reference axis at an angle of about 90 degrees.

39. The medical infusion device of claim 30, wherein said primary fluid inlet port and said primary fluid outlet port are disposed along a first reference axis extending along said primary fluid flow passageway, and wherein said infusion port and said check valve opening are disposed along a second reference which intersects with said first reference axis at an acute less than about 90 degrees.

40. The medical infusion device of claim 30, wherein said a check valve chamber, said check valve support structure, said primary fluid inlet port, said primary fluid outlet port, and said infusion port are made from an optically transparent plastic.

41. The medical infusion device of claim 40, wherein said optically transparent plastic is polycarbonate.

42. The medical infusion device of claim 31, wherein said flexible check valve disc is made from silicone rubber.

43. The medical infusion device of claim 42, wherein said medical fluid supply means is a needleless injection syringe containing a supply of said medical fluid and connectable to said infusion port by way of said third connector.

44. The medical infusion device of claim 30, in combination with (1) a catheter for introducing said primary intravenous stream into the body of a patient, (2) a first section of flexible medical tubing having a first end connectable to said catheter and a second end connectable to said primary fluid outlet port, and (3) a second section of flexible medical tubing having a first end connectable to said medical fluid supply means and a second end connectable to said primary fluid inlet port.

45. A medical infusion device for infusing a medical fluid into a primary fluid stream, comprising:

(1) a check valve chamber having an interior volume, surrounded by a chamber wall surface of three dimensional extent, a check valve opening formed through said chamber wall surface, a check valve chamber opening formed through said chamber wall surface and axially aligned with said check valve opening, and first and second primary fluid flow openings formed through said chamber wall surface;

(2) a flexible check valve element;

(3) a check valve support structure for supporting said flexible check valve element against said check valve opening in a normally closed configuration preventing the flow of fluid through said check valve opening in said normally closed configuration, said check valve support structure further including a base portion for closing off said check valve chamber opening in a sealed manner;

(4) a primary fluid inlet port for connecting said medical infusion device to a first connector capable of providing a primary fluid stream, said primary fluid inlet port further including a primary fluid inlet opening and a primary fluid inlet flow passageway extending from said primary fluid inlet opening through said first primary fluid flow passageway and into the interior volume of said check valve chamber;

(5) a primary fluid outlet port for connecting said medical infusion device to a second connector capable of receiving said primary fluid stream, said primary fluid outlet port further including a primary fluid outlet opening and a primary fluid outlet flow passageway extending from said primary fluid outlet flow opening through said second primary fluid flow passageway and into the interior volume of said check valve chamber;

(6) a primary fluid flow passageway continuously extending from said primary fluid inlet port to said primary fluid outlet port by way of passage through said primary fluid inlet opening, said primary fluid inlet flow passageway, said first primary fluid flow opening, said interior volume of said check valve chamber, said second primary fluid flow opening, said primary fluid outlet flow passageway, and said primary fluid outlet opening;

(7) an infusion port for connecting said medical infusion device to a third connector operably connected to a medical fluid supply means for supplying medical fluid through said third connector for infusion into said primary fluid stream, said infusion port further including an infusion fluid inlet opening, and an infusion fluid inlet flow passageway extending from said infusion fluid inlet opening through said check valve opening into the interior volume of said check valve chamber; and (8) a check valve plunger disposed along said infusion fluid inlet flow passageway adjacent said check valve opening, and being displaceable along said infusion port in response to slidable engagement by said actuator so that said check valve plunger engages said flexible check valve element and reconfigures said flexible check valve element from said normally closed configuration into an open configuration permitting said medical fluid to flow from said medical fluid supply means through said infusion fluid inlet port, along said infusion fluid inlet flow passageway, through said check valve opening, and into said primary fluid stream passing along said primary fluid flow passageway.

46. The medical infusion device of claim 45, wherein said flexible check valve element is a flexible check valve disc, and said check valve opening comprises a circular opening and an annular surface extending about said circular opening and facing the interior volume of said check valve chamber, and wherein said flexible check valve disc has an upper surface that engages said annular surface when said flexible check valve disc is configured in said normally closed configuration.

47. The medical infusion device of claim 46, wherein said circular opening is disposed within a plane, and said check valve support structure extends substantially perpendicular to said plane and engages said central portion of said flexible check valve disc when said flexible check valve disc is configured in said normally closed configuration.

48. The medical infusion device of claim 47, wherein said check valve opening comprises a check valve bar disposed substantially within said plane and extending across said circular opening so as to bisect the same, and wherein said flexible check valve disc is supported between said check valve support element, said annular surface and said check valve bar when said flexible check valve disc is configured in said normally closed configuration.

49. The medical infusion device of claim 48, wherein said check valve support element has a width dimension of substantially planar geometry and said check valve bar has a width dimension of substantially planar geometry, and wherein said check valve element and said check valve bar are arranged so that the width dimension of said check valve support element is aligned with the width dimension of said check valve bar to form a thin planar region.

50. The medical infusion device of claim 49, wherein said first and second primary fluid flow openings are disposed along a primary fluid flow axis extending through the interior of said check valve chamber and the thin planar region within which said check valve support element is disposed.

51. The medical infusion device of claim 48, wherein said check valve support structure further comprises a base portion having a substantially planar top fluid-flow surface, from which said check valve support element extends.

52. The medical infusion device of claim 51, wherein said check valve support element comprises a triangular structure having a base, and two side surfaces extending from said base and converging towards a tip portion which engages the central portion of said flexible check valve disc.

53. The medical infusion device of claim 46, wherein said check valve plunger includes a tubular portion having a longitudinal extent and for sliding along a portion of said infusion fluid inlet flow passageway, and a check valve disc engaging means associated with said tubular portion for engaging said upper surface of said flexible check valve disc so as to reconfigure said flexible check valve disc in said open configuration when the actuator of said third connector engages and displaces said check valve plunger towards said check valve opening.

54. The medical infusion device of claim 53, wherein said infusion fluid inlet flow passageway has a substantially cylindrical geometry, and said check valve plunger has a longitudinal extent, and wherein said check valve disc engaging means comprises a pair of prong-like elements extending from said tubular portion along said longitudinal extent, and each said prong-like element terminating in projection extending radially outward in a direction substantially perpendicular to said longitudinal axis.

55. The medical infusion device of claim 45, wherein said a check valve chamber, said check valve support structure, said primary fluid inlet port, said primary fluid outlet port, and said infusion port are made from an optically transparent plastic.

56. The medical infusion device of claim 55, wherein said optically transparent plastic is polycarbonate.

57. The medical infusion device of claim 45, wherein said flexible check valve disc is made from silicone rubber.

58. The medical infusion device of claim 57, wherein said medical fluid supply means is a needleless injection syringe containing a supply of said medical fluid and connectable to said infusion port by way of said third connector.

59. The medical infusion device of claim 45, in combination with (1) a catheter for introducing said primary intravenous stream into the body of a patient, (2) a first section of flexible medical tubing having a first end connectable to said catheter and a second end connectable to said primary fluid outlet port, and (3) a second section of flexible medical tubing having a first end connectable to said medical fluid supply means and a second end connectable to said primary fluid inlet port.

60. A medical infusion device for infusing a medical fluid into a primary fluid stream, comprising:

(1) a check valve chamber having an interior volume, surrounded by a chamber wall surface of three dimensional extent, a check valve opening formed through said chamber wall surface, a check valve chamber opening formed through said chamber wall surface and axially aligned with said check valve opening, and a first primary fluid flow opening formed through said chamber wall surface;

(2) a flexible check valve element;

(3) a check valve support structure for supporting said flexible check valve element against said check valve opening in a normally closed configuration, for preventing the flow of fluid through said check valve opening on said normally closed configuration, said check valve support structure further including a base portion for closing off said check valve chamber opening in a sealed manner, and a second primary fluid flow opening formed in said base portion;

(4) a primary fluid inlet port for connecting said medical infusion device to a first connector capable of providing a primary fluid stream, said primary fluid inlet port further including a primary fluid inlet opening and a primary fluid inlet flow passageway extending from said primary fluid inlet opening through said first primary fluid flow passageway and into the interior volume of said check valve chamber;

(5) a primary fluid outlet port for connecting said medical infusion device to a second connector capable of receiving said primary fluid stream, said primary fluid outlet port further including a primary fluid outlet opening and a primary fluid outlet flow passageway extending from said primary fluid outlet flow opening through said second primary fluid flow passageway and into the interior volume of said check valve chamber;

(6) a primary fluid flow passageway continuously extending from said primary fluid inlet port to said primary fluid outlet port by way of passage through said primary fluid inlet opening, said primary fluid inlet flow passageway, said first primary fluid flow opening, said interior volume of said check valve chamber, said second primary fluid flow opening, said primary fluid outlet flow passageway, and said primary fluid outlet opening;

(7) an infusion port for connecting said medical infusion device to a third connector operably connected to a medical fluid supply means for supplying medical fluid through said third connector for infusion into said primary fluid stream, said infusion port further including an infusion fluid inlet opening, and an infusion fluid inlet flow passageway extending from said infusion fluid inlet opening through said check valve opening into the interior volume of said check valve chamber; and (8) a check valve plunger disposed along said infusion fluid inlet flow passageway adjacent said check valve opening, and being displaceable along said infusion fluid inlet flow passageway in response to slidable engagement by said actuator so that said check valve plunger engages said flexible check valve element and reconfigures said flexible check valve element from said normally closed configuration into an open configuration permitting said medical fluid to flow from said medical fluid supply means through said infusion fluid inlet port, along said infusion fluid inlet flow passageway, through said check valve opening, and into said primary fluid stream passing along said primary fluid flow passageway.

61. The medical infusion device of claim 60, wherein said flexible check valve element is a flexible check valve disc, and said check valve opening comprises a circular opening and an annular surface extending about said circular opening and facing the interior volume of said check valve chamber, and wherein said flexible check valve disc has an upper surface that engages said annular surface when said flexible check valve disc is configured in said normally closed configuration.

62. The medical infusion device of claim 61, wherein said circular opening is disposed within a plane, and said check valve support structure extends substantially perpendicular to said plane and engages said central portion of said flexible check valve disc when said flexible check valve disc is configured in said normally closed configuration.

63. The medical infusion device of claim 62, wherein said check valve opening comprises a check valve bar disposed substantially within said plane and extending across said circular opening so as to bisect the same, and wherein said flexible check valve disc is supported between said check valve support element, said annular surface and said check valve bar when said flexible check valve disc is configured in said normally closed configuration.

64. The medical infusion device of claim 63, wherein said check valve support element has a width dimension of substantially planar geometry and said check valve bar has a width dimension of substantially planar geometry, and wherein said check valve support element and said check valve bar are arranged so that the width dimension of said check valve support element is aligned with the width dimension of said check valve bar to form a thin planar region.

65. The medical infusion device of claim 64, wherein said first and second primary fluid flow openings are disposed along a primary fluid flow axis extending through the interior of said check valve chamber and the thin planar region within which check valve support element is disposed.

66. The medical infusion device of claim 63, wherein said check valve support structure further comprises a base portion having a substantially planar top fluid-flow surface, from which said check valve support element extends.

67. The medical infusion device of claim 66, wherein said check valve support element comprises a triangular structure having a base, and two side surfaces extending from said base and converging towards a tip portion which engages the central portion of said flexible check valve disc.

68. The medical infusion device of claim 61, wherein said check valve plunger includes a tubular portion having a longitudinal extent and for sliding along a portion of said infusion fluid inlet flow passageway, and a check valve disc engaging means associated with said tubular portion for engaging said upper surface of said flexible check valve disc so as to reconfigure said flexible check valve disc in said open configuration when the actuator of said third connector engages and displaces said check valve plunger towards said check valve opening.

69. The medical infusion device of claim 68, wherein said infusion fluid inlet flow passageway has a substantially cylindrical geometry, and said check valve plunger has a longitudinal extent, and wherein said check valve disc engaging means comprises a pair of prong-like elements extending from said tubular portion along said longitudinal extent, and each said prong-like element terminating in projection extending radially outward in a direction substantially perpendicular to said longitudinal axis.

70. The medical infusion device of claim 60, wherein said a check valve chamber, said check valve support structure, said primary fluid inlet port, said primary fluid outlet port, and said infusion port are made from an optically transparent plastic.

71. The medical infusion device of claim 70, wherein said optically transparent plastic is polycarbonate.

72. The medical infusion device of claim 60, wherein said flexible check valve disc is made from silicone rubber.

73. The medical infusion device of claim 60, in combination with (1) a catheter for introducing said primary intravenous stream into the body of a patient, (2) a first section of flexible medical tubing having a first end connectable to said catheter and a second end connectable to said primary fluid outlet port, and (3) a second section of flexible medical tubing having a first end connectable to said medical fluid supply means and a second end connectable to said primary fluid inlet port.

74. A medical infusion device for infusing a medical fluid into a primary fluid stream, comprising:

(1) a plurality of check valve chambers, each said check valve chamber having an interior volume, surrounded by a chamber wall surface of three dimensional extent, a check valve opening formed through said chamber wall surface, a check valve chamber opening formed through said chamber wall surface and axially aligned with said check valve opening, first and second primary fluid flow openings, a flexible check valve element having a normally closed configuration and an open configuration; a check valve support structure for supporting said flexible check valve element said check valve opening in said normally closed configuration preventing the flow of fluid through said check valve opening in said normally closed configuration;

(2) a primary fluid inlet port for connecting said medical infusion device to a first connector capable of providing a primary fluid stream, said primary fluid inlet port further including a primary fluid inlet opening and a primary fluid inlet flow passageway extending from said primary fluid inlet opening through said first primary fluid flow passageway and into the interior volume of said check valve chamber;

(3) a primary fluid outlet port for connecting said medical infusion device to a second connector capable of receiving said primary fluid stream, said primary fluid outlet port further including a primary fluid outlet opening and a primary fluid outlet flow passageway extending from said primary fluid outlet flow opening through said second primary fluid flow passageway and into the interior volume of said check valve chamber;

(4) a primary fluid flow passageway continuously extending from said primary fluid inlet port to said primary fluid outlet port by way of passage through said primary fluid inlet opening, said primary fluid inlet flow passageway, said first primary fluid flow opening, said interior volume of said check valve chamber, said second primary fluid flow opening, said primary fluid outlet flow passageway, and said primary fluid outlet opening;

(5) a plurality of infusion ports, each said infusion port being capable of connecting said medical infusion device to an infusion connector operably connected to a medical fluid supply means for supplying medical fluid through said infusion connector for infusion into said primary fluid stream, each infusion port further including an infusion fluid inlet opening, and an infusion fluid inlet flow passageway extending from said infusion fluid inlet opening through said check valve opening into the interior volume of said check valve chamber; and wherein, when said flexible check valve element is arranged in said open configuration, each said infusion connector is connected to one said infusion port, and one said medical fluid supply means supplies medical fluid through one said infusion connector, said medical fluid flows from one said medical fluid supply means through one said infusion fluid inlet port, along one said infusion fluid inlet flow passageway, through one said check valve opening, and therefrom directly into said primary fluid stream passing along said primary fluid flow passageway.

75. The medical infusion device of claim 74, wherein each said flexible check valve element is a flexible check valve disc, and each said check valve opening comprises a circular opening and an annular surface extending about said circular opening and facing the interior volume of said check valve chamber, and wherein each said flexible check valve disc has an upper surface that engages said annular surface when said flexible check valve disc is configured in said normally closed configuration.

76. The medical infusion device of claim 75, wherein each said circular opening is disposed within a plane, and each said check valve support structure extends substantially perpendicular to said plane and engages said central portion of said flexible check valve disc when said flexible check valve disc is configured in said normally closed configuration.

77. The medical infusion device of claim 76, wherein each said check valve opening comprises a check valve bar disposed substantially within said plane and extending across said circular opening so as to bisect the same, and wherein each said flexible check valve disc is supported between said check valve support element, said annular surface and said check valve bar when said flexible check valve disc is configured in said normally closed configuration.

78. The medical infusion device of claim 77, wherein each said check valve support element has a width dimension of substantially planar geometry and each said check valve bar has a width dimension of substantially planar geometry, and wherein said check valve element and said check valve bar are arranged so that the width dimension of said check valve support element is aligned with the width dimension of said check valve bar to form a thin planar region.

79. The medical infusion device of claim 78, wherein said first and second primary fluid flow openings of each said check valve chamber are disposed along a primary fluid flow axis extending through the interior of said check valve chamber and the thin planar region within which said check valve support element is disposed.

80. The medical infusion device of claim 77, wherein each said check valve support structure further comprises a base portion having a substantially planar top fluid-flow surface, from which said check valve support element extends.

81. The medical infusion device of claim 80, wherein each said check valve support element comprises a triangular structure having a base, and two side surfaces extending from said base and converging towards a tip portion which engages the central portion of said flexible check valve disc.

82. The medical infusion device of claim 74, wherein said primary fluid inlet port and said primary fluid outlet port are disposed along a first reference axis extending along said primary fluid flow passageway, and wherein each said infusion port and each said check valve opening are disposed along a second reference which intersects with said first reference axis at an angle of about 90 degrees.

83. The medical infusion device of claim 74, wherein said a check valve chamber, said check valve support structure, said primary fluid inlet port, said primary fluid outlet port, and said infusion port are made from an optically transparent plastic.

84. The medical infusion device of claim 83, wherein said optically transparent plastic is polycarbonate.

85. The medical infusion device of claim 74, wherein said flexible check valve disc is made from silicone rubber.

86. The medical infusion device of claim 74, in combination with (1) a catheter for introducing said primary intravenous stream into the body of a patient, (2) a first section of flexible medical tubing having a first end connectable to said catheter and a second end connectable to said primary fluid outlet port, and (3) a second section of flexible medical tubing having a first end connectable to said medical fluid supply means and a second end connectable to said primary fluid inlet port.

* * * * *